(12) United States Patent
Kim

(10) Patent No.: US 10,858,670 B2
(45) Date of Patent: Dec. 8, 2020

(54) **NANO-VESICLES DERIVED FROM GENUS *MORGANELLA* BACTERIA AND USE THEREOF**

(71) Applicant: MD HEALTHCARE INC., Seoul (KR)

(72) Inventor: Yoon-Keun Kim, Paju (KR)

(73) Assignee: MD HEALTHCARE INC., Seoul (KR)

(*) Notice: Subject to any disclaimer, the term of this patent is extended or adjusted under 35 U.S.C. 154(b) by 0 days.

(21) Appl. No.: 16/399,919

(22) Filed: Apr. 30, 2019

(65) Prior Publication Data

US 2019/0249197 A1 Aug. 15, 2019

Related U.S. Application Data

(63) Continuation-in-part of application No. PCT/KR2018/016494, filed on Dec. 21, 2018.

(30) Foreign Application Priority Data

| Jan. 12, 2018 | (KR) | 10-2018-0004603 |
| Dec. 10, 2018 | (KR) | 10-2018-0158636 |

(51) Int. Cl.

| C12N 15/88 | (2006.01) |
| C12N 15/82 | (2006.01) |
| C12Q 1/686 | (2018.01) |
| A61K 39/00 | (2006.01) |
| A61K 45/00 | (2006.01) |
| C12R 1/01 | (2006.01) |
| C12Q 1/06 | (2006.01) |
| C12Q 1/6886 | (2018.01) |
| A61K 9/127 | (2006.01) |
| A61K 35/74 | (2015.01) |
| C12N 1/20 | (2006.01) |
| C12Q 1/689 | (2018.01) |

(52) U.S. Cl.
CPC ............ *C12N 15/88* (2013.01); *A61K 9/1271* (2013.01); *A61K 35/74* (2013.01); *C12N 1/20* (2013.01); *C12Q 1/06* (2013.01); *C12Q 1/686* (2013.01); *C12Q 1/689* (2013.01); *C12Q 1/6886* (2013.01); *C12R 1/01* (2013.01)

(58) Field of Classification Search
CPC .... C12N 15/88; C12N 15/8257; A61K 38/00; A61K 39/39; C12Q 1/686
See application file for complete search history.

(56) References Cited

U.S. PATENT DOCUMENTS

| 2002/0028215 A1* | 3/2002 | Kadurugamuwa | ......................... A61K 47/6901 424/234.1 |
| 2010/0233195 A1* | 9/2010 | Delisa | .................... C12N 15/11 424/184.1 |
| 2012/0093869 A1* | 4/2012 | Klumpp | .................. A61P 31/04 424/257.1 |
| 2016/0113881 A1* | 4/2016 | Sosin | ..................... A61K 39/35 424/497 |

FOREIGN PATENT DOCUMENTS

| KR | 10-2011-0025068 A | 3/2011 |
| KR | 10-2015-0133646 A | 11/2015 |
| KR | 10-1833348 B1 | 3/2018 |
| KR | 10-1833502 B1 | 3/2018 |
| KR | 10-2018-0077067 A | 7/2018 |
| KR | 10-2018-0077070 A | 7/2018 |
| KR | 10-2018-0098154 A | 9/2018 |
| WO | 2016-133324 A1 | 8/2016 |
| WO | 2017-009693 A1 | 1/2017 |
| WO | 2018-008895 A1 | 1/2018 |

OTHER PUBLICATIONS

Kim et al., Journal of Food Protection, 2003; 66(8): 1385-1392 (Year: 2003).*
Cancer Treatment Centers of America, https://www.cancercenter.com/cancer-types/pancreatic-cancer/, accessed Jun. 8, 2020. (Year: 2020).*
Ilic et al., World Journal of Gastroenterology, 2016; 22(44): 9694-9705 (Year: 2016).*

(Continued)

*Primary Examiner* — Gary B Nickol
*Assistant Examiner* — Lakia J Jackson-Tongue
(74) *Attorney, Agent, or Firm* — Lucas & Mercanti, LLP

(57) ABSTRACT

The present invention relates to vesicles derived from genus *Morganella* bacteria and a use thereof, the present inventors experimentally confirmed that the vesicles were significantly decreased in clinical samples derived from patients with a malignant disease such as gastric cancer, colorectal cancer, pancreatic cancer, bile duct cancer, breast cancer, ovarian cancer, bladder cancer, prostate cancer and lymphoma, a cardiovascular disease such as myocardial infarction, cardiomyopathy, atrial fibrillation, variant angina, and stroke, diabetes mellitus, and Parkinson's disease as compared to normal persons, and the vesicles suppressed the secretion of inflammatory mediators by pathogenic vesicles and suppressed the occurrence of cancer, so that the vesicles derived from genus *Morganella* bacteria may be usefully used for the purpose of developing a method for diagnosing a malignant disease such as gastric cancer, colorectal cancer, pancreatic cancer, bile duct cancer, breast cancer, ovarian cancer, bladder cancer, prostate cancer and lymphoma, a cardiovascular disease such as myocardial infarction, cardiomyopathy, atrial fibrillation, variant angina, and stroke, diabetes mellitus, and Parkinson's disease, and a composition for preventing or treating the diseases or an inflammatory disease.

10 Claims, 30 Drawing Sheets

Specification includes a Sequence Listing.

(56) References Cited

OTHER PUBLICATIONS

Wang et al., 2015, "Neuroinflammation in Parkinson's disease and its potential as therapeutic target," Translational Neurodegeneration, 4:19 p. 1-9.
Qiao et al., The change of serum tumor necrosis factor alpha in patients with type 1 diabetes mellitus: A systematic review and meta-analysis, PLOS ONE, 2017, https://doi.org/10.1371/journal.pone.0176157.
Akash et al., Jan. 2018, Tumor necrosis factor-alpha: Role in development of insulin resistance and pathogenesis of type 2 diabetes mellitus, Journal of Cellular Biochemistry,119(1):105-110. doi: 10.1002/jcb.26174. Epub Jun. 22, 2017.
Jordan et al., 2008, Inflammation as Therapeutic Objective in Stroke, Current Pharmaceutical Design, pp. 3549-3564, vol. 14 No. 33.
Guo et al., 2012, Inflammation in Atrial Fibrillation, Journal of the American College of Cardiology, pp. 2263-2270, vol. 60 No. 22.
Harada et al., Role of Inflammation in Atrial Fibrillation Pathophysiology and Management, US Dept. of Health and Human Services HHS Public Access, 2016, Published in final edited form as: Circ J. 2015; 79(3): 495-502. doi:10.1253/circj.CJ-15-0138.
Palomer et al., Oct. 9, 2013, An overview of the crosstalk between inflammatory processes and metabolic dysregulation during diabetic cardiomyopathy, International Journal of Cardiology, 168(4):3160-72. doi: 10.1016/j.jcard.2013.07.150. Epub Aug. 6, 2013.
Tian et al., Tumor necrosis factor-a and its role as a mediator in myocardial infarction: A brief review, Chronic Diseases and Translational Medicine, 2015, pp. 18-26, vol. 1.
Bartekova et al., Role of cytokines and inflammation in heart function during health and disease, Heart Failure Reviews, 2018, pp. 733-758, vol. 23.
Berry et al., TNF-alpha in asthma, Current Opinion in Pharmacology, 2007, pp. 279-282, vol. 7.
Pellissier et al., Relationship between Vagal Tone, Cortisol, TNF-Alpha, Epinephrine and Negative Affects in Crohn's Disease and Irritable Bowel Syndrome, 2014, PLOS ONE, p. 1-9, vol. 9 issue 9 e105328.
Betsi et al., 2008, Probiotics for the Treatment or Prevention of Atopic Dermatitis A Review of the Evidence from Randomized Controlled Trials, American Journal of Clinical Dermatology, pp. 93-103, vol. 9 No. 2.
Tanni et al., 2010, Smoking status and tumor necrosis factor-alpha mediated systemic inflammation in COPD patients, Journal of Inflammation,7:29, http://www.journal-inflammation.com/content/7/1/29.
Sriram et al., 2007, Divergent Roles for Tumor Necrosis Factor-alpha in the Brain, Journal Neuroimmune Pharmacol, 2007, pp. 140-153, vol. 2.
Skinnider et al., 2002, The role of cytokines in classical Hodgkin lymphoma, BLOOD journal, pp. 4283-4297, vol. 99 No. 12.
Bardia et al., 2009, Anti-inflammatory drugs, antioxidants, and prostate cancer prevention, Curr Opin Pharmacol, 9(4): 419-426.
Sethi et al., 2008, TNF: A master switch for inflammation to cancer, Frontiers in Bioscience, pp. 5094-5107.
Wu et al., 2010,TNF-a/NF-kB/Snail pathway in cancer cell migration and invasion, British Journal of Cancer, pp. 639-644, vol. 102.
Techasen et al., 2012, Cytokines Released from Activated Human Macrophages Induce Epithelial Mesenchymal Transition Markers of Cholangiocarcinoma Cells, Asian Pacific Journal of Cancer Prevention, pp. 115-118, vol. 13.
Balkwill et al., 2012, Cancer-related inflammation: Common themes and therapeutic opportunities, Seminars in Cancer Biology, pp. 33-40, vol. 22.
Triantafillidis et al., 2009, Colorectal Cancer and Inflammatory Bowel Disease: Epidemiology, Risk Factors, Mechanisms of Carcinogenesis and Prevention Strategies, Anticancer Research, pp. 2727-2738, vol. 29.
Landskron et al., 2014, Chronic Inflammation and Cytokines in the Tumor Microenvironment, Journal of Immunology Research, vol. 2014 Article ID 149185 http://dx.doi.org/10.1155/2014/149185.
International Search Report for PCT/KR2018/016494, dated Apr. 22, 2019.

* cited by examiner

```
                     SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)..(42)
<223> OTHER INFORMATION: n is a, c, g, or t

<400> SEQUENCE: 1
tcgtcggcag cgtcagatgt gtataagaga cagcctacgg gnggcwgcag            50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc      55
```

NANO-VESICLES DERIVED FROM GENUS *MORGANELLA* BACTERIA AND USE THEREOF

CROSS-REFERENCE TO RELATED APPLICATIONS

This application is a Continuation in Part of PCT/KR2018/016494, filed Dec. 21, 2018, which claims the benefit of priority from Korean Patent Application No. 10-2018-0004603, filed Jan. 12, 2018 and Korean Patent Application No. 10-2018-0158636, filed Dec. 10, 2018, the contents of each of which are incorporated herein by reference.

FIELD OF THE INVENTION

The present invention relates to nano-vesicles derived from genus *Morganella* bacteria, and a use thereof, and more particularly, to a method for diagnosing a malignant disease such as gastric cancer, colorectal cancer, pancreatic cancer, bile duct cancer, breast cancer, ovarian cancer, bladder cancer, prostate cancer and lymphoma, a cardiovascular disease such as myocardial infarction, cardiomyopathy, atrial fibrillation, variant angina, and stroke, diabetes mellitus, and Parkinson's disease by using nano-vesicles derived from genus *Morganella* bacteria, and a composition for preventing or treating the disease or an inflammatory disease including the vesicles.

BACKGROUND OF THE INVENTION

Since the beginning of the 21st century, acute infectious diseases recognized as epidemic diseases in the past have become less important, whereas chronic diseases accompanied by immune dysfunction caused by disharmony between humans and microbiomes have changed disease patterns as main diseases that determine the quality of life and the human lifespan. As an intractable chronic disease in the 21st century, cancer, cardiovascular diseases, chronic lung diseases, metabolic diseases, inflammatory diseases, and neuropsychiatric diseases have become a big problem for public health in the country as main diseases that determine the human lifespan and the quality of life.

Inflammation is a local or systemic protective mechanism against the damage or infection of cells and tissues, and is typically caused by a serial biological response occurring as humoral mediators that constitute the immune system directly respond to the damage or infection, or stimulate the local or systemic effector system. Examples of a main inflammatory disease include digestive diseases such as gastritis and inflammatory enteritis, oral diseases such as periodontitis, respiratory diseases such as asthma, chronic obstructive pulmonary disease (COPD), and rhinitis, arthritis such as degenerative arthritis and rheumatoid arthritis, and metabolic diseases such as obesity, diabetes mellitus, and hepatic sclerosis. Further, various studies have reported that persistent inflammation may cause cancer.

It is known that the number of microorganisms coexisting in the human body has reached 100 trillion, which is 10 times more than the number of human cells, and the number of microorganism genes is more than 100 times the number of human genes. A microbiota or microbiome refers to a microbial community including bacteria, archaea and eukarya present in a given habitat.

Bacteria coexisting in our body and bacteria present in the ambient environment secrete nanometer-sized vesicles in order to exchange information on genes, low molecular compounds, proteins, and the like with other cells. The mucosa forms a physical defense membrane through which particles having a size of 200 nanometers (nm) or more cannot pass, so that bacteria coexisting in the mucosa cannot pass through the mucosa, but vesicles derived from bacteria have a size of 100 nanometers or less and are absorbed into our bodies after relatively freely passing through epithelial cells via the mucosa.

Locally secreted bacterial-derived vesicles not only are absorbed through mucosal epithelial cells or skin keratinocytes to induce local inflammatory responses but also are absorbed into our bodies to be distributed to respective organs and regulate immune and inflammatory responses in the organ that absorbs the vesicles. For example, vesicles derived from pathogenic gram-negative bacteria such as *Escherichia coli* promote a systemic inflammatory response and blood coagulation through vascular endothelial cell inflammatory responses when absorbed by blood vessels, and are also absorbed into muscular cells where insulin acts to cause insulin resistance and diabetes mellitus. In contrast, vesicles derived from beneficial bacteria may regulate diseases by regulating immune functions and metabolic dysfunctions by pathogenic vesicles (Choi)(W et al., Gut microbe-derived extracellular vesicles induce insulin resistance, thereby impairing glucose metabolism in skeletal muscle. Scientific Reports, 2015.).

Immune responses to factors such as vesicles derived from bacteria are Th17 immune responses characterized by the secretion of IL-17 cytokines, and IL-6 is secreted when exposed to vesicles derived from bacteria, thereby inducing Th17 immune responses. Inflammation caused by a Th17 immune response is characterized by infiltration of neutrophils, and TNF-alpha, which is secreted from inflammatory cells such as macrophages, plays an important role in the process by which inflammation occurs.

Genus *Morganella* bacteria are anaerobic gram-negative rod-shaped bacteria and are known as bacteria coexisting in the intestines of humans and animals. Among these bacteria, *Morganella morganii* bacteria are known as pathogenic bacteria causing infection after surgery, urinary tract infection, and the like. However, the fact that genus *Morganella* bacteria secrete vesicles out of the cells has not been reported so far, and in particular, there have been no cases where the vesicles are applied to the diagnosis and treatment of cancer, cardiovascular diseases, metabolic diseases, inflammatory diseases, and neuropsychiatric diseases.

Thus, in the present invention, it was confirmed that a disease could be diagnosed by confirming that vesicles derived from genus *Morganella* bacteria were significantly decreased in clinical samples of patients with cancer, cardiovascular diseases, metabolic diseases, inflammatory diseases, and neuropsychiatric diseases as compared to normal persons. Further, as a result of isolating vesicles from *Morganella morganii* bacteria and analyzing the characteristics thereof, it was confirmed that the vesicles could be used as a composition for preventing or treating a malignant disease, a cardiovascular disease, a metabolic disease, an inflammatory disease, and a neuropsychiatric disease.

As a result of intensive studies to solve the conventional problems as described above, the present inventors confirmed that through metagenomic analysis, the content of vesicles derived from genus *Morganella* bacteria was significantly decreased in clinical samples from patients with a malignant disease such as gastric cancer, colorectal cancer, pancreatic cancer, bile duct cancer, breast cancer, ovarian cancer, bladder cancer, prostate cancer and lymphoma, a cardiovascular disease such as myocardial infarction, cardiomyopathy, atrial fibrillation, variant angina, and stroke, diabetes mellitus, and Parkinson's disease as compared to normal persons. In addition, it was confirmed that when macrophages were treated with vesicles isolated from *Morganella morganii* bacteria belonging to genus *Morganella*, the secretion of TNF-alpha caused by pathogenic vesicles was remarkably suppressed, and the present invention based on this finding is completed.

Thus, an object of the present invention is to provide a method for providing information for diagnosing gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, or Parkinson's disease.

Further, another object of the present invention is to provide a composition for preventing or treating gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, Parkinson's disease, or an inflammatory disease, including *Morganella*-derived vesicles as an active ingredient.

However, a technical problem to be achieved by the present invention is not limited to the aforementioned problems, and the other problems that are not mentioned may be clearly understood by a person skilled in the art from the following description.

SUMMARY OF THE INVENTION

To achieve the object of the present invention as described above, the present invention provides a method for providing information for diagnosing gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, or Parkinson's disease, the method including the following steps:

(a) extracting DNAs from vesicles isolated from samples of a normal person and a subject;

(b) obtaining each PCR product by performing PCR using a primer pair constructed based on a gene sequence present in 16S rDNA for the extracted DNAs; and (c) determining a case where a content of vesicles derived from genus *Morganella* bacteria is lower than that of the normal person through a quantitative analysis of the PCR product as gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, or Parkinson's disease.

In addition, the present invention provides a method for diagnosing gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, or Parkinson's disease, the method including the following steps:

(a) extracting DNAs from vesicles isolated from samples of a normal person and a subject;

(b) obtaining each PCR product by performing PCR using a primer pair constructed based on a gene sequence present in 16S rDNA for the extracted DNAs; and (c) determining a case where a content of vesicles derived from genus *Morganella* bacteria is lower than that of the normal person through a quantitative analysis of the PCR product as gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, or Parkinson's disease.

As another exemplary embodiment of the present invention, the sample in Step (a) may be blood, urine, or stool.

As still another exemplary embodiment of the present invention, the primer pair in Step (b) may be primers of SEQ ID Nos. 1 and 2.

Further, the present invention provides a pharmaceutical composition for preventing or treating one or more diseases selected from the group consisting of gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, Parkinson's disease, and an inflammatory disease, including vesicles derived from genus *Morganella* bacteria as an active ingredient.

In addition, the present invention provides a food composition for preventing or alleviating one or more diseases selected from the group consisting of gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, Parkinson's disease, and an inflammatory disease, including vesicles derived from genus *Morganella* bacteria as an active ingredient.

Furthermore, the present invention provides a method for preventing or treating one or more diseases selected from the group consisting of gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, Parkinson's disease, and an inflammatory disease, the method including a step of administering a pharmaceutical composition including vesicles derived from genus *Morganella* bacteria as an active ingredient to a subject.

Further, the present invention provides a use of vesicles derived from genus *Morganella* bacteria for preventing or treating one or more diseases selected from the group consisting of gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, Parkinson's disease, and an inflammatory disease.

As an exemplary embodiment of the present invention, the inflammatory disease may be one or more selected from the group consisting of atopic dermatitis, acne, psoriasis, sinusitis, rhinitis, conjunctivitis, asthma, dermatitis, inflammatory collagen vascular disease, glomerulonephritis, encephalitis, inflammatory enteritis, chronic obstructive pulmonary disease, sepsis, septic shock, pulmonary fibrosis, undifferentiated spondyloarthropathy, undifferentiated arthropathy, arthritis, inflammatory osteolysis, a chronic inflammatory disease caused by viral or bacterial inflammation, colitis, ulcerative colitis, inflammatory bowel disease, arthritis, rheumatoid arthritis, reactive arthritis, osteoarthritis, scleriasis, osteoporosis, atherosclerosis, myocarditis, endocarditis, pericarditis, cystic fibrosis, Hashimoto's thyroiditis, Grave's disease, leprosy, syphilis, Lyme disease, borreliosis, neuro-borreliosis, tuberculosis, sarcoidosis, lupus, chilblain lupus, tuberculosis lupus, lupus nephritis, systemic lupus erythematosus, macular degeneration, uveitis, irritable bowel syndrome, Crohn's disease, Sjogren syndrome, fibromyalgia, chronic fatigue syndrome, chronic fatigue immune dysfunction syndrome, myalgic encephalomyelitis, amyotrophic lateral sclerosis, Parkinson's disease, and multiple sclerosis.

As another exemplary embodiment of the present invention, the inflammatory disease may be a disease mediated by IL-6 or TNF-α.

As still another exemplary embodiment of the present invention, the vesicles may have an average diameter of 10 to 200 nm.

As yet another exemplary embodiment of the present invention, the vesicles may be secreted naturally or artificially from genus *Morganella* bacteria.

As yet another exemplary embodiment of the present invention, the vesicles derived from genus *Morganella* bacteria may be secreted from *Morganella morganii*.

The present inventors confirmed that intestinal bacteria are not absorbed into the body, but vesicles derived from bacteria are absorbed into the body through epithelial cells, systemically distributed, and excreted from the body through the kidneys, liver, and lungs, and that through a metagenomic analysis of vesicles derived from bacteria present in the blood, urine, stool, or the like of a patient, vesicles derived from genus *Morganella* bacteria present in the blood, urine, or stool of patients with gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, and Parkinson's disease had been significantly decreased as compared to those in normal persons.

Further, it was observed that when vesicles were isolated by culturing *Morganella morganii* which is one species of genus *Morganella* bacteria in vitro and administered to inflammatory cells in vitro, the secretion of inflammatory mediators by pathogenic vesicles was significantly suppressed and the occurrence of cancer was suppressed in a cancer animal model, so that it is expected that vesicles derived from genus *Morganella* bacteria according to the present invention can be usefully used for a method for diagnosing gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, and Parkinson's disease, and a composition for preventing or treating the disease or inflammatory disease, such as a food or a drug against the disease or inflammatory disease.

DETAILED DESCRIPTION OF THE INVENTION

Figure 1A:
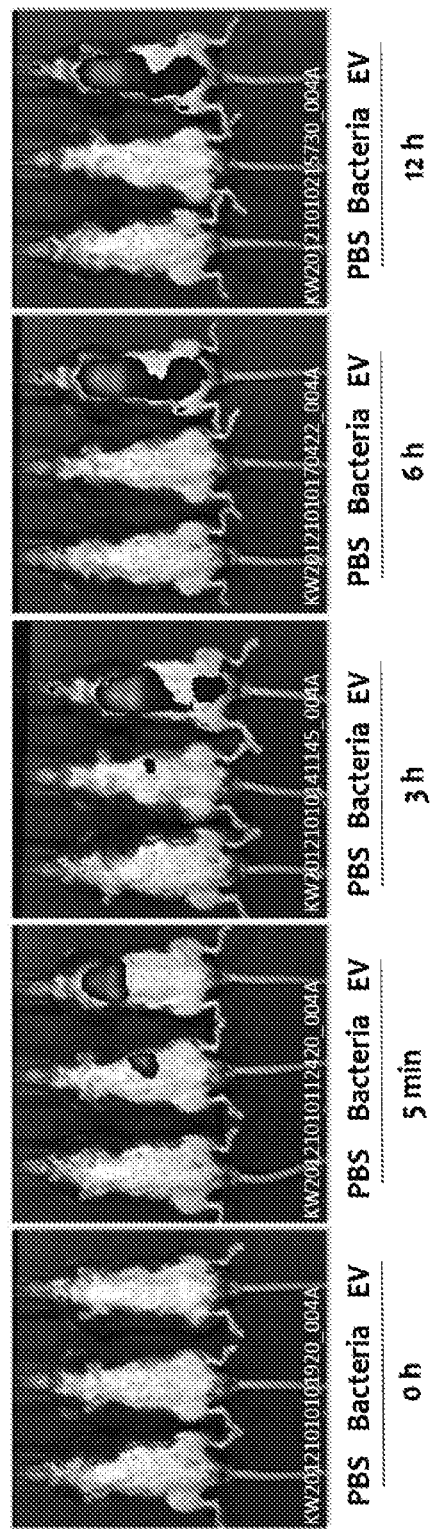
FIG. 1A is a series of photographs capturing distribution patterns of bacteria and vesicles derived from bacteria (EV) by time after the bacteria and the vesicles derived from bacteria were orally administered to mice.

The present invention relates to vesicles derived from genus *Morganella* bacteria and a use thereof.

The present inventors confirmed that through a metagenomic analysis, the content of vesicles derived from genus *Morganella* bacteria was remarkably reduced in samples from patients with gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, and Parkinson's disease as compared to normal persons, thereby completing the present invention based on this.

Thus, the present invention provides a method for providing information for diagnosing gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, or Parkinson's disease, the method including the following steps:

(a) extracting DNAs from vesicles isolated from samples of a normal person and a subject;

(b) obtaining each PCR product by performing PCR using a primer pair constructed based on a gene sequence present in 16S rDNA for the extracted DNAs; and (c) determining a case where a content of vesicles derived from genus *Morganella* bacteria is lower than that of the normal person through a quantitative analysis of the PCR product as gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, or Parkinson's disease.

The term "diagnosis" as used herein refers to determination of a condition of a disease of a patient over all aspects, in a broad sense. The contents of the determination are the disease entity, the etiology, the pathogenesis, the severity, the detailed aspects of a disease, the presence and absence of complications, the prognosis, and the like. The diagnosis in the present invention means determining whether gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, and Parkinson's disease occur, the level of the disease, and the like.

The term "nanovesicle" or "vesicle" as used herein refers to a structure consisting of a nano-sized membrane secreted from various bacteria.

Vesicles derived from gram-negative bacteria or outer membrane vesicles (OMVs) have not only endotoxins (lipopolysaccharides) but also toxic proteins and bacterial DNA and RNA, and vesicles derived from gram-positive bacteria also have peptidoglycan and lipoteichoic acid which are cell wall components of bacteria in addition to proteins and nucleic acids. In the present invention, nanovesicles or vesicles are secreted naturally from genus *Morganella* bacteria or produced artificially, are in the form of a sphere, and have an average diameter of 10 to 200 nm.

The vesicles may be isolated from a culturing solution including genus *Morganella* bacteria by using one or more methods selected from the group consisting of centrifugation, ultra-high speed centrifugation, high pressure treatment, extrusion, sonication, cell lysis, homogenization, freezing-thawing, electroporation, mechanical decomposition, chemical treatment, filtration by a filter, gel filtration chromatography, free-flow electrophoresis, and capillary electrophoresis. Further, a process such as washing for removing impurities and concentration of obtained vesicles may be further included.

The term "metagenome" as used herein also refers to a microbiome, and refers to a total of genomes including all viruses, bacteria, fungi, and the like in an isolated region such as soil and an animal's intestines, and is typically used as a concept of genomes explaining identification of a large number of microorganisms at one time by using a sequence analyzer in order to analyze uncultivated microorganisms. In particular, the metagenome does not refer to a genome of one species, but refers to a kind of mixed genome as a genome of all species of one environmental unit. The metagenome is, when one species is defined in the development process of omics biology, a term derived from the viewpoint of making a complete species is made by various species interacting with each other as well as one kind of functionally existing species. Technically, the metagenome is an object of a technique to identify all species in one environment and investigate interactions and metabolism by analyzing all DNAs and RNAs regardless of species using a rapid sequence analysis method.

In the present invention, the sample in Step (a) may be blood, urine, or stool, but is not limited thereto.

In the present invention, the primer pair in Step (b) may be primers of SEQ ID Nos. 1 and 2.

As another aspect of the present invention, the present invention provides a pharmaceutical composition for preventing or treating one or more diseases selected from the group consisting of gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, Parkinson's disease, and an inflammatory disease, including vesicles derived from genus *Morganella* bacteria as an active ingredient.

As still another aspect of the present invention, the present invention provides a food composition for preventing or alleviating one or more diseases selected from the group consisting of gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, Parkinson's disease, and an inflammatory disease, including vesicles derived from genus *Morganella* bacteria as an active ingredient.

In the present invention, the inflammatory disease may be one or more selected from the group consisting of atopic dermatitis, acne, psoriasis, sinusitis, rhinitis, conjunctivitis, asthma, dermatitis, inflammatory collagen vascular disease, glomerulonephritis, encephalitis, inflammatory enteritis, chronic obstructive pulmonary disease, sepsis, septic shock, pulmonary fibrosis, undifferentiated spondyloarthropathy, undifferentiated arthropathy, arthritis, inflammatory osteolysis, a chronic inflammatory disease caused by viral or bacterial inflammation, colitis, ulcerative colitis, inflammatory bowel disease, arthritis, rheumatoid arthritis, reactive arthritis, osteoarthritis, scleriasis, osteoporosis, atherosclerosis, myocarditis, endocarditis, pericarditis, cystic fibrosis, Hashimoto's thyroiditis, Grave's disease, leprosy, syphilis, Lyme disease, borreliosis, neuro-borreliosis, tuberculosis, sarcoidosis, lupus, chilblain lupus, tuberculosis lupus, lupus nephritis, systemic lupus erythematosus, macular degeneration, uveitis, irritable bowel syndrome, Crohn's disease, Sjogren syndrome, fibromyalgia, chronic fatigue syndrome, chronic fatigue immune dysfunction syndrome, myalgic encephalomyelitis, amyotrophic lateral sclerosis, Parkinson's disease, and multiple sclerosis, but is not limited thereto.

In the present invention, the inflammatory disease may be a disease mediated by interleukin-6 (IL-6) or tumor necrosis factor-alpha (TNF-α), but is not limited thereto.

The term "prevention" as used herein refers to all actions that suppress cancer, an inflammatory disease, a cardiovascular disease, a metabolic disease, or a neuropsychiatric disease or delay the onset thereof via administration of the food or pharmaceutical composition according to the present invention.

The term "treatment" as used herein refers to all actions that alleviate or beneficially change symptoms of cancer, an inflammatory disease, a cardiovascular disease, a metabolic disease, or a neuropsychiatric disease or delay the onset thereof via administration of the food or pharmaceutical composition according to the present invention.

The term "alleviation" used as used herein refers to all actions that at least reduce a parameter associated with a condition to be treated, for example, the degree of symptoms.

In an exemplary embodiment of the present invention, it was confirmed that by orally administering bacteria and vesicles derived from bacteria to mice to evaluate the in vivo absorption, distribution, and excretion patterns of the bacteria and the vesicles, the bacteria were not absorbed through the intestinal mucosa, whereas the vesicles were absorbed within 5 minutes, systemically distributed, and excreted through the kidneys, the liver, and the like (see Example 1).

In another exemplary embodiment of the present invention, a bacterial metagenomic analysis was performed by using vesicles isolated from the blood, urine, or stool of normal persons who were matched in age and sex with patients with gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, or Parkinson's disease. As a result, it was confirmed that vesicles derived from genus *Morganella* bacteria were significantly decreased in samples of patients with gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, or Parkinson's disease as compared to samples of normal persons (see Examples 3 to 15).

In still another exemplary embodiment of the present invention, as a result of evaluating the degree of apoptosis after treating Raw 264.7 cells which are mouse macrophages with vesicles derived from *Morganella morganii* (MMR101, MMR201, MMR202) at various concentrations (0.1, 1, 10 μg/ml) in order to evaluate apoptotic effects of vesicles derived from *Morganella morganii* (*M. morganii* EV) in inflammatory cells, it was confirmed that the apoptosis was not observed during the treatment with vesicles derived from *Morganella morganii* (MMR101, MMR201, MMR202) (see Example 17).

In yet another exemplary embodiment of the present invention, as a result of further studies to analyze characteristics of vesicles derived from species *Morganella morganii* bacteria belonging to genus *Morganella* bacteria based on the results in the Examples, the *Morganella morganii* strains were cultured and it was evaluated whether vesicles secreted from the strains exhibited anti-inflammatory effects, and as a result of evaluating the secretion of inflammatory mediators by treating macrophages with vesicles derived from *Escherichia coli* which is a causative factor after treating the macrophages with vesicles derived from *Morganella morganii*, it was confirmed that the vesicles derived from *Morganella morganii* efficiently suppressed the secretion of IL-6 and TNF-α by vesicles derived from *Escherichia coli* (see Example 18).

In yet another exemplary embodiment of the present invention, as a result of evaluating effects of heat treatment or acid treatment on the secretion of TNF-α by administering heat-treated or acid-treated vesicles before treating macrophages with vesicles derived from *Escherichia coli* in order to evaluate effects of heat treatment or acid treatment on anti-inflammatory actions of vesicles derived from *Morganella morganii*, it was confirmed that effects of suppressing the secretion of TNF-α by vesicles derived from *Morganella morganii* were not changed (see Example 19).

In yet another embodiment of the present invention, the *Morganella morganii* strains were cultured and it was evaluated whether vesicles secreted from the strains exhibited anti-cancer treatment effects. For this purpose, a cancer model was prepared by subcutaneously injecting a cancer cell line and as a result of measuring the size of cancer tissues for 20 days after orally or intraperitoneally administering vesicles derived from *Morganella morganii* to mice from 4 days before the treatment of the cancer cell line, it was confirmed that when the vesicles were intraperitoneally and orally administered, the size of cancer tissues was decreased as compared to that of a control, and particularly, when the vesicles were orally administered, the size of cancer tissues was remarkably decreased (see Example 20).

The pharmaceutical composition of the present invention may include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in the Remington's literature. The pharmaceutical composition of the present invention is not particularly limited in formulation, but may be formulated into an injection, an inhalant, an external preparation for skin, an oral ingestion, or the like.

The pharmaceutical composition of the present invention may be orally administered or may be parenterally administered (for example, administered intravenously, subcutaneously, intradermally, intranasally, or the intratracheally) according to the target method, and the administration dose may vary depending on the patient's condition and body weight, severity of disease, drug form, and administration route and period, but may be appropriately selected by those of ordinary skill in the art.

The pharmaceutical composition according to the present invention is administered in a pharmaceutically effective amount. In the present invention, the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields. The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

Specifically, the effective amount of the pharmaceutical composition according to the present invention may vary depending on the patient's age, sex, and body weight, and generally, 0.001 to 150 mg of the composition and preferably, 0.01 to 100 mg of the composition, per 1 kg of body weight, may be administered daily or every other day or may be administered once to three times a day. However, since the effective amount may be increased or decreased depending on the administration route, the severity of obesity, the gender, the body weight, the age, and the like, the administration dose is not intended to limit the scope of the present invention in any way.

The food composition of the present invention includes a health functional food composition. The food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials.

However, for long-term intake for the purpose of health and hygiene or for the purpose of health control, the amount may be less than the above-mentioned range.

Other ingredients are not particularly limited, except that the food composition of the present invention contains the active ingredient as an essential ingredient at the indicated ratio, and the food composition of the present invention may contain various flavorants, natural carbohydrates, and the like, like a typical beverage, as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, stevia extract (for example, rebaudioside A, glycyrrhizin and the like), and a synthetic flavorant (saccharin, aspartame and the like) may be advantageously used. The proportion of the natural carbohydrate may be appropriately determined by the choice of those of ordinary skill in the art.

The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by those of ordinary skill in the art.

EXAMPLES

Hereinafter, preferred Examples for helping the understanding of the present invention will be suggested. However, the following Examples are provided only to more easily understand the present invention, and the contents of the present invention are not limited by the following Examples.

Example 1. Analysis of In Vivo Absorption, Distribution, and Excretion Patterns of Intestinal Bacteria and Vesicles Derived from Bacteria In order to evaluate whether intestinal bacteria and vesicles derived from bacteria were systemically absorbed through the gastrointestinal tract, an experiment was performed with the following method. A dose of 50 μg of each of intestinal bacteria and vesicles derived from intestinal bacteria labeled with fluorescence in the stomach of a mouse were administered to the gastrointestinal tract, and fluorescence was measured after 0 minute, 5 minutes, 3 hours, 6 hours, and 12 hours. As a result of observing the entire image of the mouse, as illustrated in FIG. 1A, the bacteria were not systemically absorbed through the intestinal mucosa, but the vesicles derived from bacteria were systemically absorbed 5 minutes after administration, and fluorescence was strongly observed in the bladder 30 minutes after administration, so that it could be seen that the vesicles were excreted to the urinary tract. Further, it could be seen that the vesicles were present in the body until 12 hours after administration (see FIG. 1A).

Figure 1B:
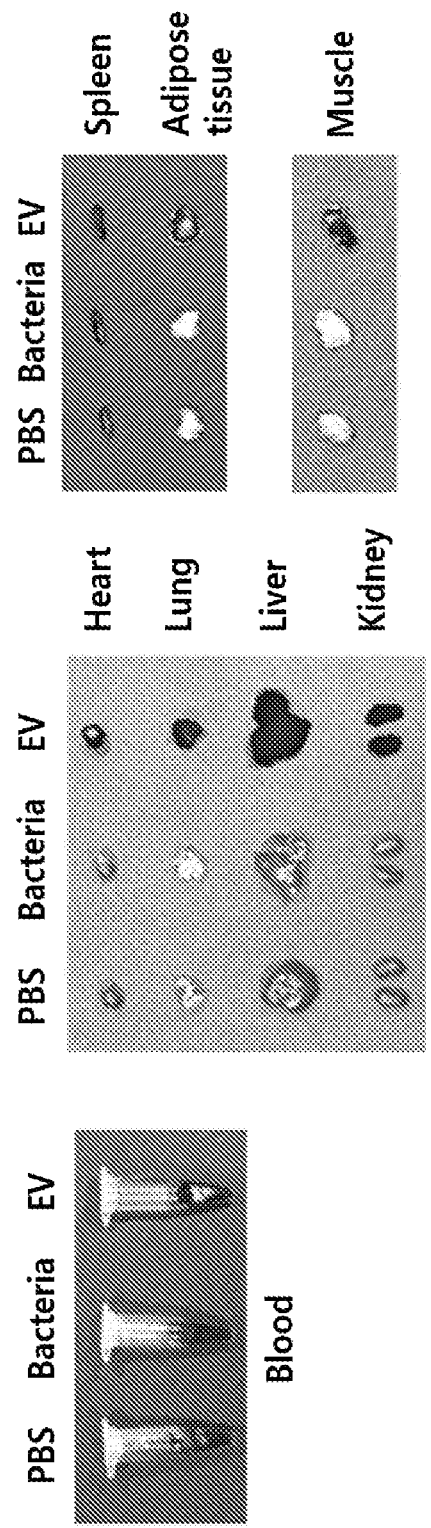
FIG. 1B is a result of evaluating the in vivo distribution patterns of the bacteria and the vesicles by harvesting blood, kidneys, liver, and various organs at 12 hours after orally administering the bacteria and the vesicles.

In order to evaluate the pattern in which the intestinal bacteria and the vesicles derived from the intestinal bacteria infiltrated into various organs after they were systemically absorbed, 50 μg of bacteria and vesicles derived from bacteria labeled with fluorescence were administered in the same manner as described above, and then the blood, heart, lungs, liver, kidneys, spleen, fat, and muscle were collected 12 hours after administration. As a result of observing fluorescence in the collected tissues, as illustrated in FIG. 1B, it could be seen that the vesicles derived from bacteria were distributed in the blood, heart, lungs, liver, kidneys, spleen, fat, and muscle, but the bacteria were not absorbed (see FIG. 1B).

Example 2. Metagenomic Analysis of Vesicles Derived from Bacteria in Clinical Sample A clinical sample such as blood, urine, or stool was first put into a 10-ml tube, suspended matter was allowed to settle down by centrifugation (3,500×g, 10 min, 4° C.), and only the supernatant was transferred to a new 10-ml tube. After bacteria and impurities were removed by using a 0.22-μm filter, they were transferred to a Centriprep tube (centrifugal filters 50 kD) and centrifuged at 1,500×g and 4° C. for 15 minutes, materials smaller than 50 kD were discarded, and the residue was concentrated to 10 ml. After bacteria and impurities were removed once again by using a 0.22-μm filter, the supernatant was discarded by using a ultra-high speed centrifugation at 150,000×g and 4° C. for 3 hours with a Type 90Ti rotor, and an aggregated pellet was dissolved in physiological saline (PBS).

Internal DNA was extracted out of the lipid by boiling 100 μl of the vesicles isolated by the above method at 100° C., and then cooled on ice for 5 minutes. And then, in order to remove the remaining suspended matter, the DNA was centrifuged at 10,000×g and 4° C. for 30 minutes, and only the supernatant was collected. And, the amount of DNA was quantified by using Nanodrop. Thereafter, in order to confirm whether the DNA derived from bacteria was present in the extracted DNA, PCR was performed with 16s rDNA primers shown in the following Table 1 and it was confirmed that genes derived from bacteria were present in the extracted genes.

TABLE 1

| primer | | Sequence | SEQ ID No. |
|---|---|---|---|
| 16S rDNA | 16S_V3_F | 5'-TCGTCGGCAGCGTCAGATGTGTATAAGAGACAGCCTACGGGNGGCWGCAG-3' | 1 |
| | 16S_V4_R | 5'-GTCTCGTGGGCTCGGAGATGTGTATAAGAGACAGGACTACHVGGGTATCTAATCC | 2 |

The DNA extracted by the above method was amplified using the 16S rDNA primers, and then sequencing was performed (Illumina MiSeq sequencer), the results were output as a standard flowgram format (SFF) file, the SFF file was converted into a sequence file (.fasta) and a nucleotide quality score file using GS FLX software (v2.9), and then the reliability estimation for the reads was confirmed, and a portion in which the window (20 bps) average base call accuracy was less than 99% (Phred score<20) was removed. For the operational taxonomy unit (OTU) analysis, clustering was performed according to sequence similarity by using UCLUST and USEARCH, the genus, family, order, class, and phylum were clustered based on 94%, 90%, 85%, 80%, and 75% sequence similarity, respectively, classification was performed at the phylum, class, order, family, and genus levels of each OUT, and bacteria having a sequence similarity of 97% or more at the genus level were profiled by using the 16S RNA sequence database (108,453 sequences) of BLASTN and GreenGenes (QIIME).

Figure 2A:
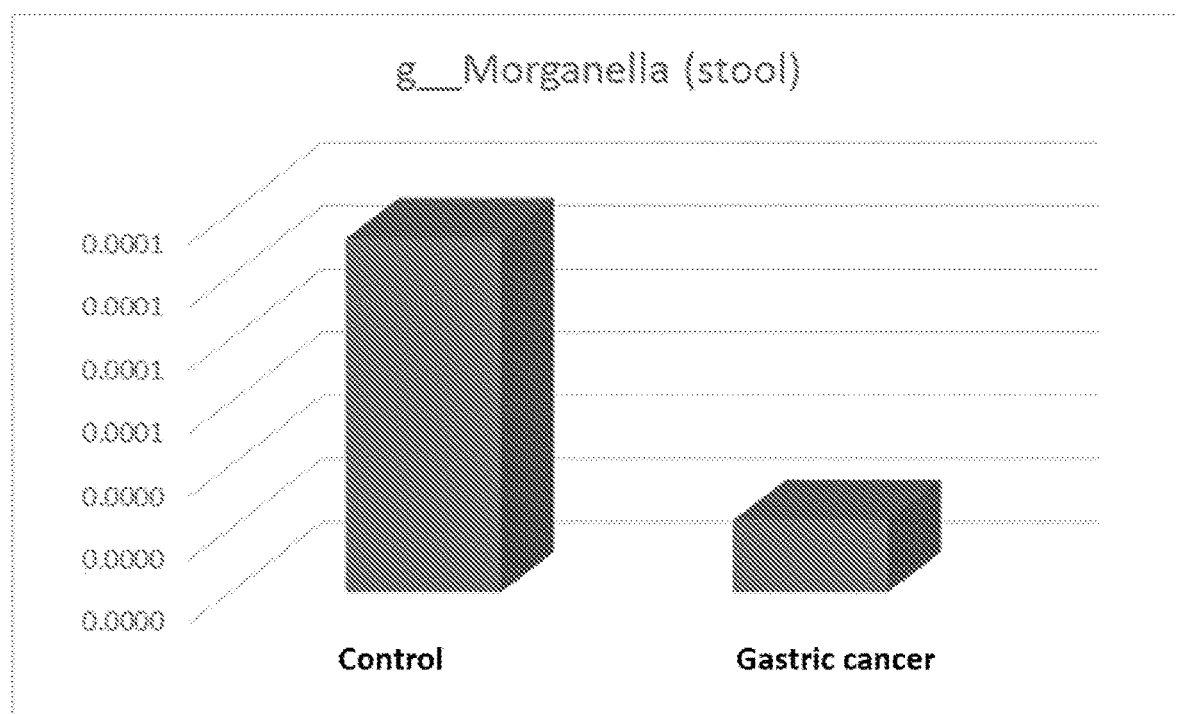
FIGS. 2A to 2C are results of comparing the distributions of vesicles derived from genus *Morganella* bacteria after performing a metagenomic analysis on vesicles derived from bacteria present in the stool (2A), blood (2B), and urine (2C) of a patient with gastric cancer and a normal person.

Example 3. Metagenomic Analysis of Vesicles Derived from Stool, Blood, and Urine Bacteria of Patient with Gastric Cancer After a metagenomic analysis was performed on the stool from 63 patients with gastric cancer and 126 normal persons who were matched in age and sex by extracting genes from vesicles present in the stool by the method in Example 2, the distribution of vesicles derived from genus *Morganella* bacteria was evaluated. As a result, it was confirmed that vesicles derived from genus *Morganella* bacteria were significantly decreased in the stool from the patients with gastric cancer as compared to the stool from the normal persons (see Table 2 and FIG. 2A).

TABLE 2

| Stool | Control | | Gastric cancer | | t-test | |
|---|---|---|---|---|---|---|
| Taxon | Mean | SD | Mean | SD | p-value | Ratio |
| g_Morganella | 0.0001 | 0.0007 | 0.0000 | 0.0002 | 0.0472 | 0.20 |

Figure 2B:
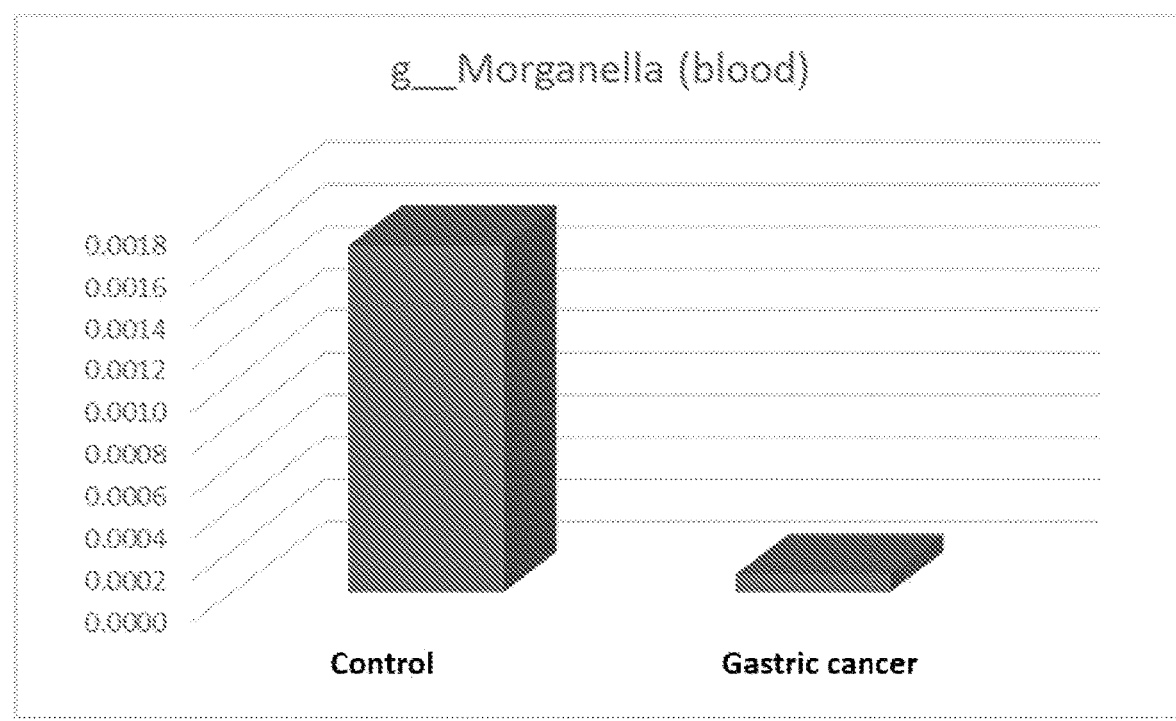

After a metagenomic analysis was performed on the blood from 66 patients with gastric cancer and 198 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with gastric cancer as compared to the blood from the normal persons (see Table 3 and FIG. 2B).

TABLE 3

| Blood | Control | | Gastric cancer | | t-test | |
|---|---|---|---|---|---|---|
| Taxon | Mean | SD | Mean | SD | p-value | Ratio |
| g_Morganella | 0.0016 | 0.0096 | 0.0001 | 0.0003 | 0.0247 | 0.05 |

Figure 2C:
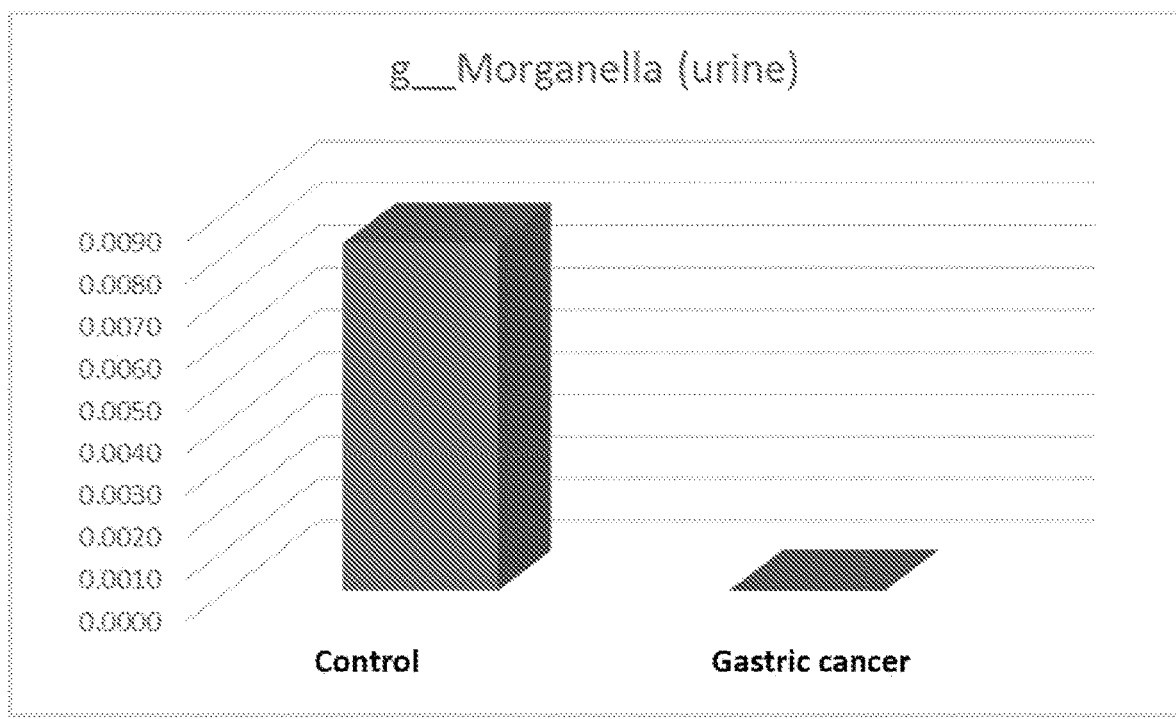

Further, after a metagenomic analysis was performed on the urine from 61 patients with gastric cancer and 120 normal persons who were matched in age and sex by extracting genes from vesicles present in the urine by the method in Example 2, the distribution of vesicles derived from genus *Morganella* bacteria was evaluated. As a result, it was confirmed that vesicles derived from genus *Morganella* bacteria were significantly decreased in the urine from the patients with gastric cancer as compared to the urine from the normal persons (see Table 4 and FIG. 2C).

TABLE 4

| Urine | Control | | Gastric cancer | | t-test | |
|---|---|---|---|---|---|---|
| Taxon | Mean | SD | Mean | SD | p-value | Ratio |
| g_Morganella | 0.0082 | 0.0217 | 0.0000 | 0.0001 | 0.0004 | 0.00 |

Figure 3:
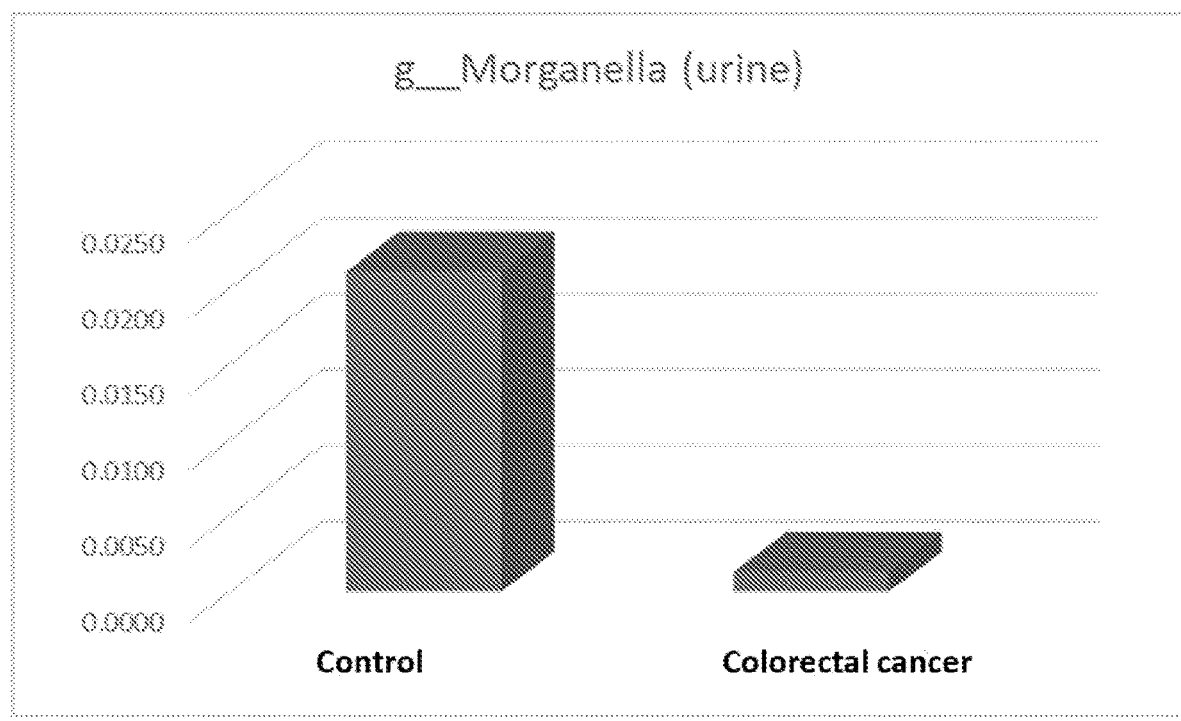
FIG. 3 is a result of comparing the distributions of vesicles derived from genus *Morganella* bacteria after performing a metagenomic analysis on vesicles derived from bacteria present in the urine of a patient with colorectal cancer and a normal person.

Example 4. Metagenomic Analysis of Vesicles Derived from Urine Bacteria of Patient with Colorectal Cancer After a metagenomic analysis was performed on the urine from 38 patients with colorectal cancer and 38 normal persons who were matched in age and sex by extracting genes from vesicles present in the urine by the method in Example 2, the distribution of vesicles derived from genus *Morganella* bacteria was evaluated. As a result, it was confirmed that vesicles derived from genus *Morganella* bacteria were significantly decreased in the urine from the patients with colorectal cancer as compared to the urine from the normal persons (see Table 5 and FIG. 3).

TABLE 5

| Urine | Control | | Colorectal cancer | | t-test | |
|---|---|---|---|---|---|---|
| Taxon | Mean | SD | Mean | SD | p-value | Ratio |
| g_Morganella | 0.0211 | 0.0295 | 0.0013 | 0.0060 | 0.0002 | 0.06 |

Figure 4:
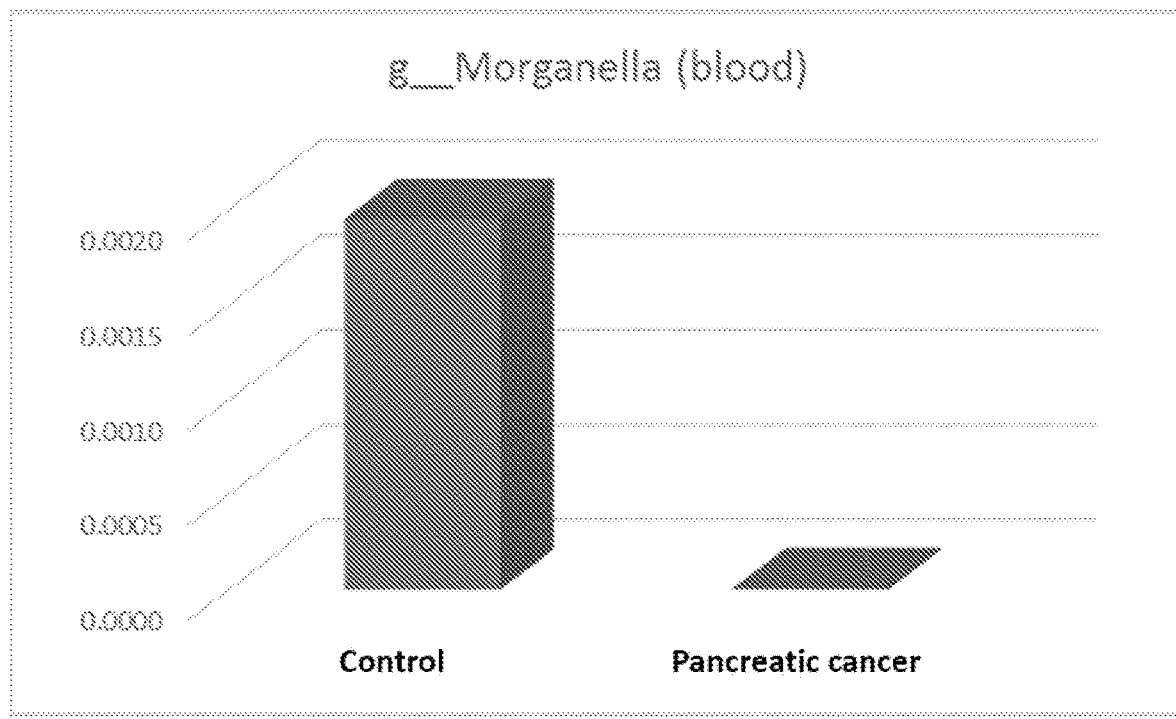
FIG. 4 is a result of comparing the distributions of vesicles derived from genus *Morganella* bacteria after performing a metagenomic analysis on vesicles derived from bacteria present in the blood of a patient with pancreatic cancer and a normal person.

Example 5. Metagenomic Analysis of Vesicles Derived from Blood Bacteria of Patient with Pancreatic Cancer After a metagenomic analysis was performed on blood from 176 patients with pancreatic cancer and 271 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with pancreatic cancer as compared to the blood from the normal persons (see Table 6 and FIG. 4).

TABLE 6

| Blood | Control | | Pancreatic cancer | | t-test | |
|---|---|---|---|---|---|---|
| Taxon | Mean | SD | Mean | SD | p-value | Ratio |
| g_Morganella | 0.0020 | 0.0088 | 0.0000 | 0.0001 | 0.0003 | 0.00 |

Figure 5:
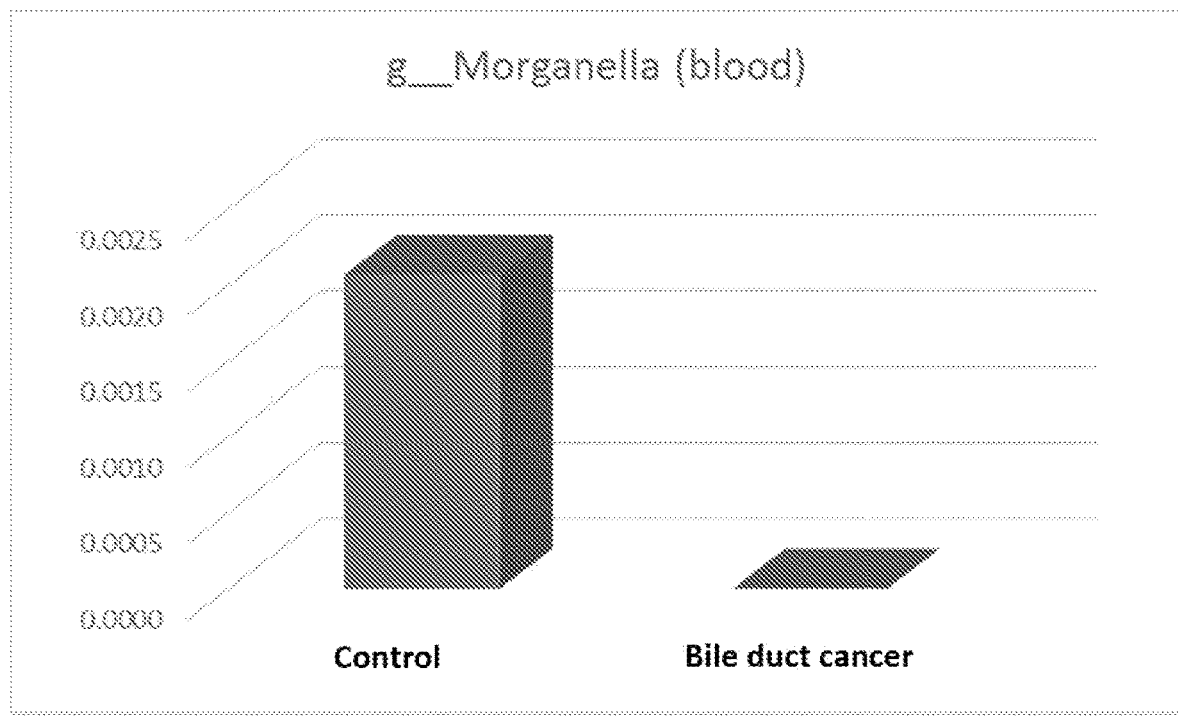
FIG. 5 is a result of comparing the distributions of vesicles derived from genus *Morganella* bacteria after performing a metagenomic analysis on vesicles derived from bacteria present in the blood of a patient with bile duct cancer and a normal person.

Example 6. Metagenomic Analysis of Vesicles Derived from Blood Bacteria of Patient with Bile Duct Cancer After a metagenomic analysis was performed on blood from 79 patients with bile duct cancer and 259 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with bile duct cancer as compared to the blood from the normal persons (see Table 7 and FIG. 5).

TABLE 7

| Blood | Control | | Bile duct cancer | | t-test | |
|---|---|---|---|---|---|---|
| Taxon | Mean | SD | Mean | SD | p-value | Ratio |
| g_Morganella | 0.0021 | 0.0091 | 0.0000 | 0.0000 | 0.0442 | 0.00 |

Figure 6:
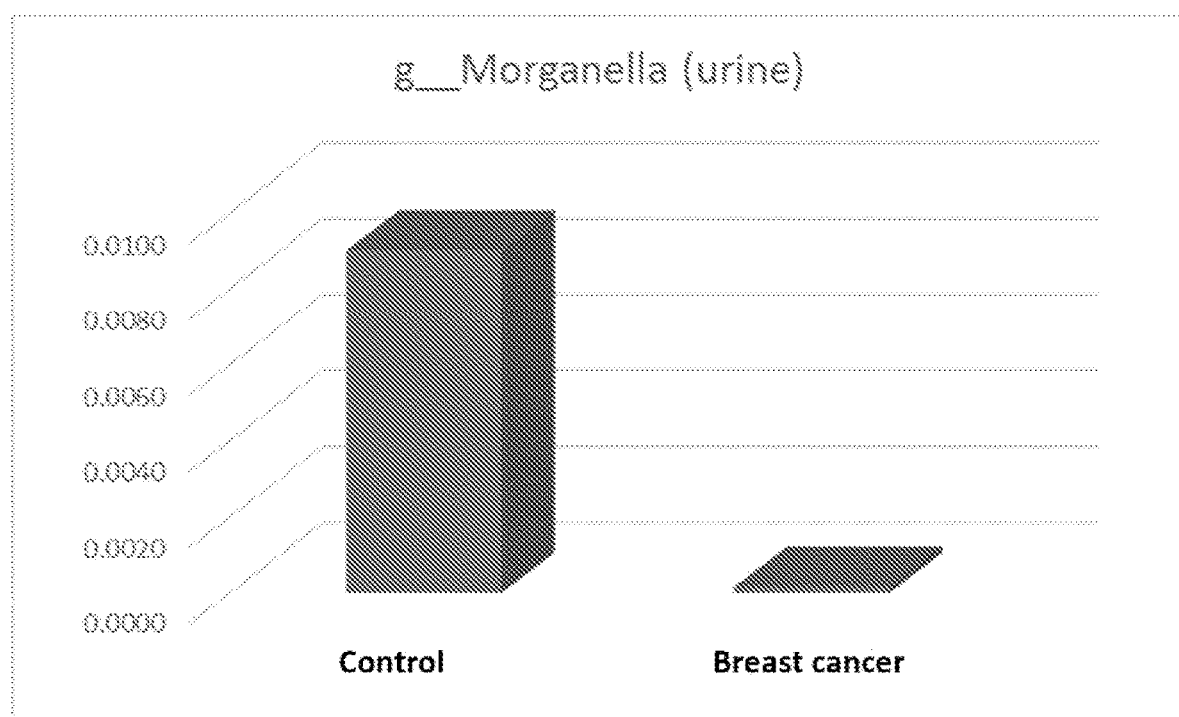
FIG. 6 is a result of comparing the distributions of vesicles derived from genus *Morganella* bacteria after performing a metagenomic analysis on vesicles derived from bacteria present in the urine of a patient with breast cancer and a normal person.

Example 7. Metagenomic Analysis of Vesicles Derived from Urine Bacteria of Patient with Breast Cancer After a metagenomic analysis was performed on urine from 127 patients with breast cancer and 220 normal persons who were matched in age and sex by extracting genes from vesicles present in the urine by the method in Example 2, the distribution of vesicles derived from genus *Morganella* bacteria was evaluated. As a result, it was confirmed that vesicles derived from genus *Morganella* bacteria were significantly decreased in the urine from the patients with breast cancer as compared to the urine from the normal persons (see Table 8 and FIG. 6).

TABLE 8

| Urine | Control | | Breast cancer | | t-test | |
|---|---|---|---|---|---|---|
| Taxon | Mean | SD | Mean | SD | p-value | Ratio |
| g_Morganella | 0.0090 | 0.0238 | 0.0002 | 0.0007 | 0.0000 | 0.02 |

Figure 7A:
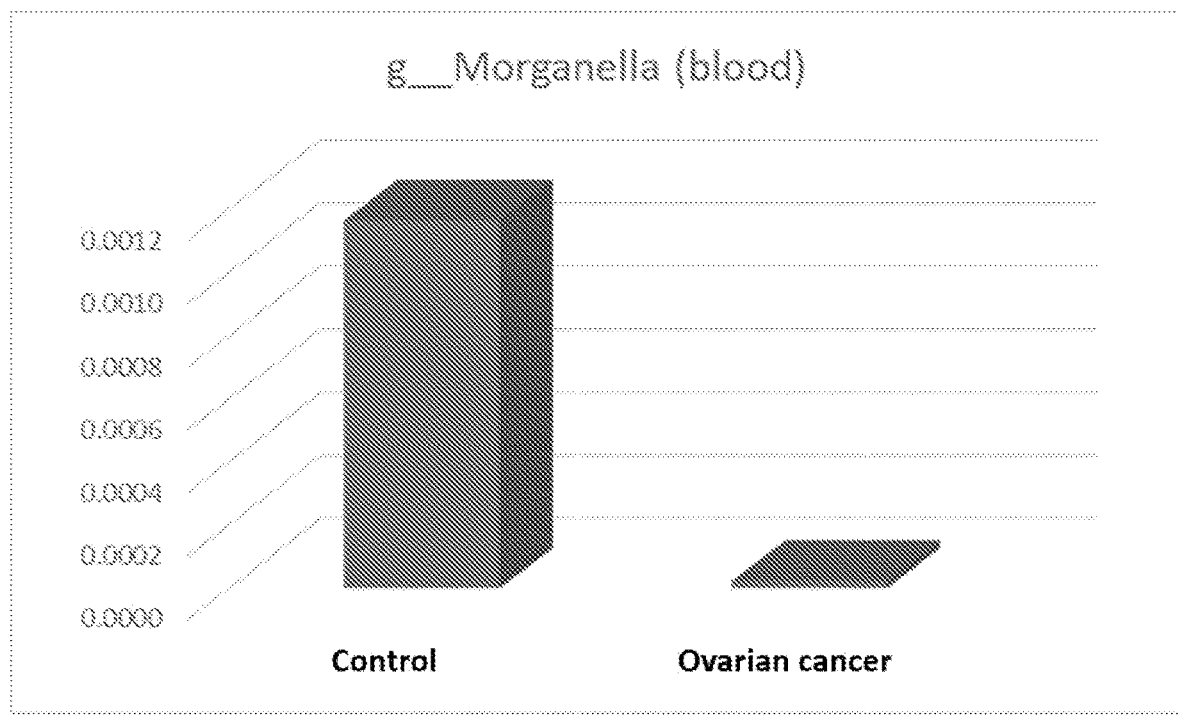
FIGS. 7A and 7B are results of comparing the distributions of vesicles derived from genus *Morganella* bacteria after performing a metagenomic analysis on vesicles derived from bacteria present in the blood (7A) and urine (7B) of a patient with ovarian cancer and a normal person.

Example 8. Metagenomic Analysis of Vesicles Derived from Blood and Urine Bacteria of Patient with Ovarian Cancer After a metagenomic analysis was performed on blood from 137 patients with ovarian cancer and 139 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with ovarian cancer as compared to the blood from the normal persons (see Table 9 and FIG. 7A).

TABLE 9

| Blood | Control | | Ovarian cancer | | t-test | |
|---|---|---|---|---|---|---|
| Taxon | Mean | SD | Mean | SD | p-value | Ratio |
| g_Morganella | 0.0012 | 0.0032 | 0.0000 | 0.0002 | 0.0000 | 0.02 |

Figure 7B:
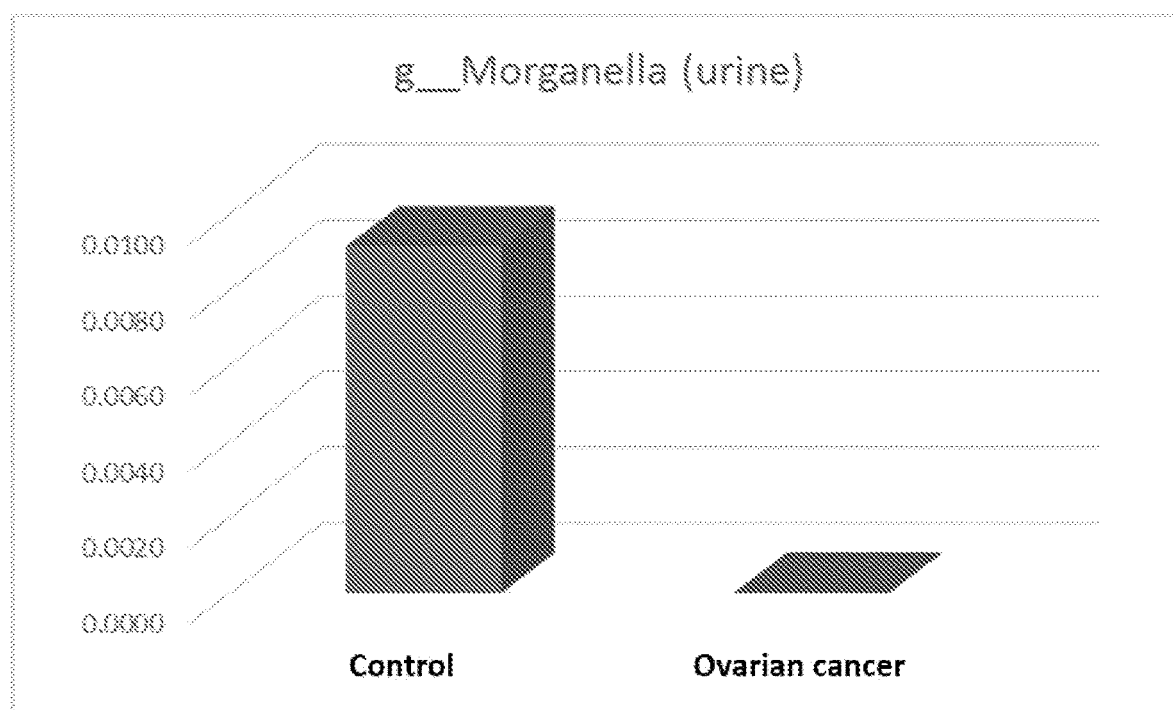

Further, after a metagenomic analysis was performed on urine from 136 patients with ovarian cancer and 136 normal persons who were matched in age and sex by extracting genes from vesicles present in the urine by the method in Example 2, the distribution of vesicles derived from genus *Morganella* bacteria was evaluated. As a result, it was confirmed that vesicles derived from genus *Morganella* bacteria were significantly decreased in the urine from the patients with ovarian cancer as compared to the urine from the normal persons (see Table 10 and FIG. 7B).

TABLE 10

| Urine | Control | | Ovarian cancer | | t-test | |
|---|---|---|---|---|---|---|
| Taxon | Mean | SD | Mean | SD | p-value | Ratio |
| g_Morganella | 0.0091 | 0.0243 | 0.0000 | 0.0002 | 0.0000 | 0.00 |

Figure 8A:
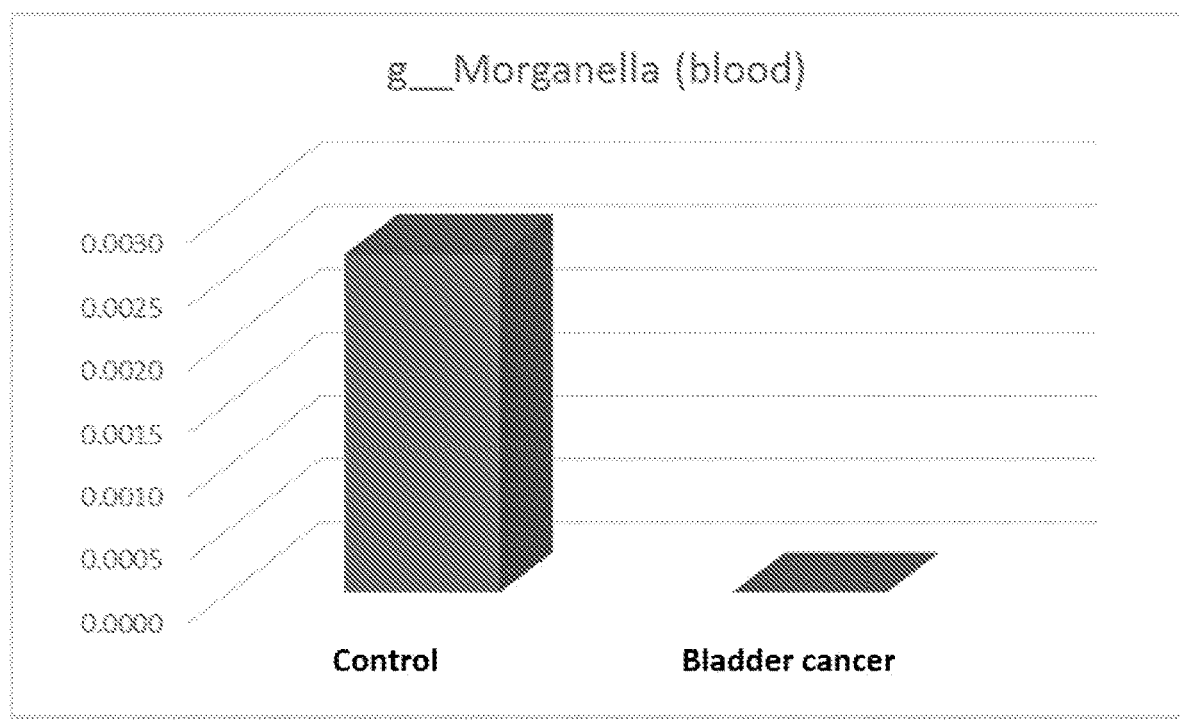
FIGS. 8A and 8B are results of comparing the distributions of vesicles derived from genus *Morganella* bacteria after performing a metagenomic analysis on vesicles derived from bacteria present in the blood (8A) and urine (8B) of a patient with bladder cancer and a normal person.

Example 9. Metagenomic Analysis of Vesicles Derived from Blood and Urine Bacteria of Patient with Bladder Cancer After a metagenomic analysis was performed on blood from 96 patients with bladder cancer and 184 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with bladder cancer as compared to the blood from the normal persons (see Table 11 and FIG. 8A).

TABLE 11

| Blood | Control | | Bladder cancer | | t-test | |
|---|---|---|---|---|---|---|
| Taxon | Mean | SD | Mean | SD | p-value | Ratio |
| g_Morganella | 0.0027 | 0.0128 | 0.0000 | 0.0000 | 0.0488 | 0.00 |

Figure 8B:
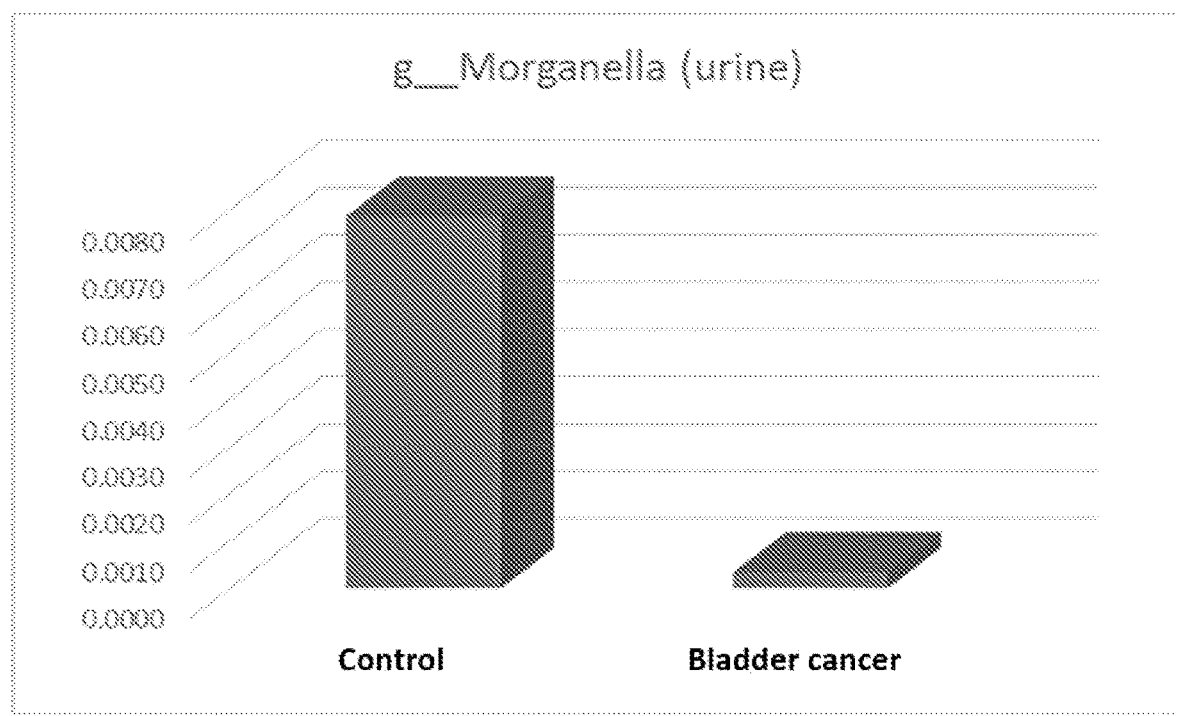

Further, after a metagenomic analysis was performed on urine from 95 patients with bladder cancer and 157 normal persons who were matched in age and sex by extracting genes from vesicles present in the urine by the method in Example 2, the distribution of vesicles derived from genus *Morganella* bacteria was evaluated. As a result, it was confirmed that vesicles derived from genus *Morganella* bacteria were significantly decreased in the urine from the patients with bladder cancer as compared to the urine from the normal persons (see Table 12 and FIG. 8B).

TABLE 12

| Urine | Control | | Bladder cancer | | t-test | |
|---|---|---|---|---|---|---|
| Taxon | Mean | SD | Mean | SD | p-value | Ratio |
| g_Morganella | 0.0079 | 0.0224 | 0.0003 | 0.0012 | 0.0009 | 0.04 |

Figure 9:
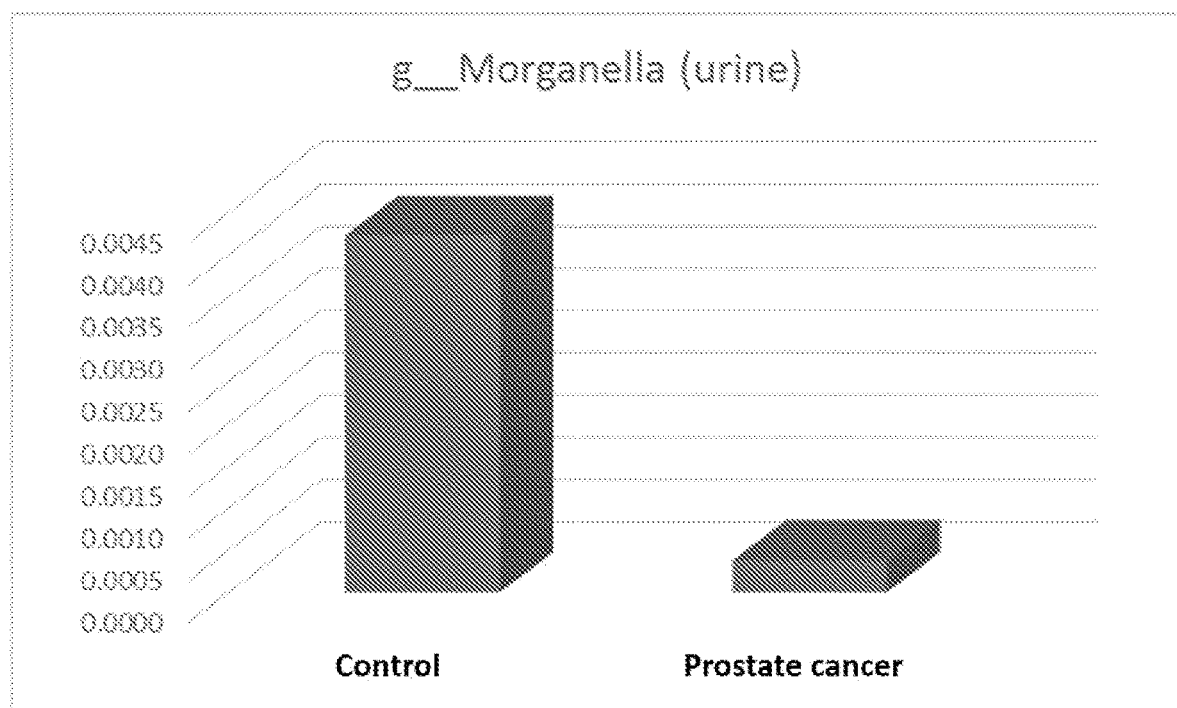
FIG. 9 is a result of comparing the distributions of vesicles derived from genus *Morganella* bacteria after performing a metagenomic analysis on vesicles derived from bacteria present in the urine of a patient with prostate cancer and a normal person.

Example 10. Metagenomic Analysis of Vesicles Derived from Urine Bacteria of Patient with Prostate Cancer After a metagenomic analysis was performed on urine from 53 patients with breast cancer and 159 normal persons who were matched in age and sex by extracting genes from vesicles present in the urine by the method in Example 2, the distribution of vesicles derived from genus *Morganella* bacteria was evaluated. As a result, it was confirmed that vesicles derived from genus *Morganella* bacteria were significantly decreased in the urine from the patients with prostate cancer as compared to the urine from the normal persons (see Table 13 and FIG. 9).

TABLE 13

| Urine | Control | | Prostate cancer | | t-test | |
|---|---|---|---|---|---|---|
| Taxon | Mean | SD | Mean | SD | p-value | Ratio |
| g_Morganella | 0.0042 | 0.0169 | 0.0004 | 0.0010 | 0.0050 | 0.09 |

Figure 10:
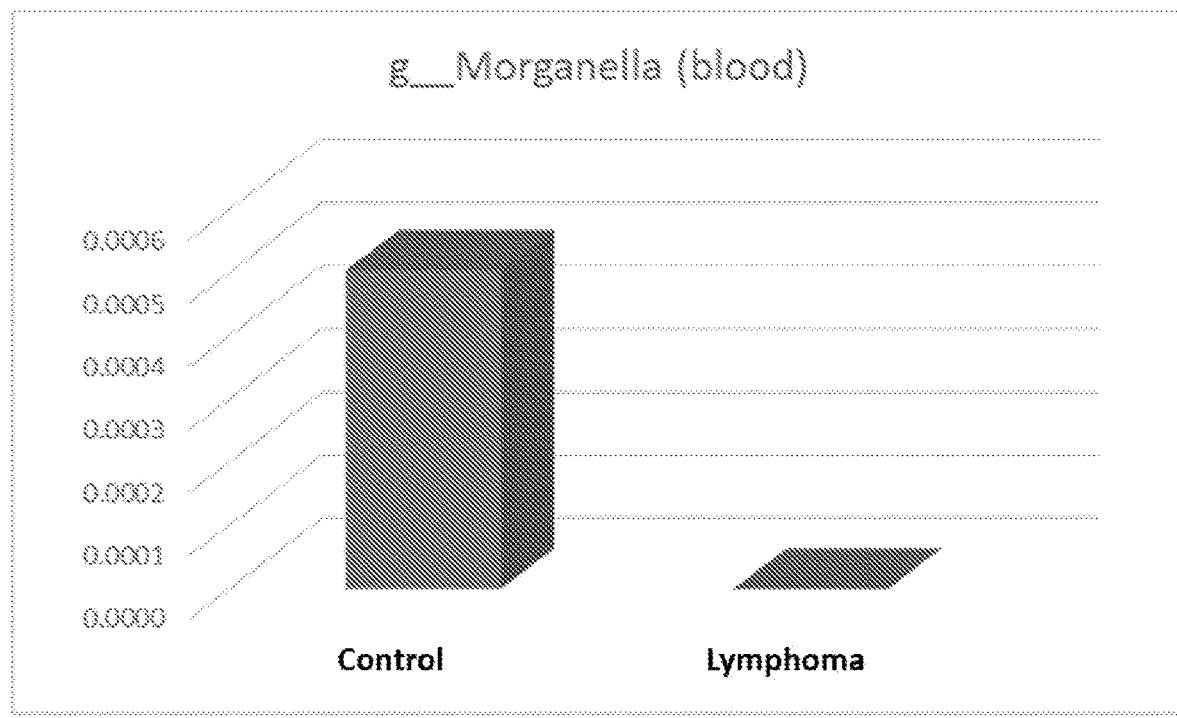
FIG. 10 is a result of comparing the distributions of vesicles derived from genus *Morganella* bacteria after performing a metagenomic analysis on vesicles derived from bacteria present in the blood of a patient with lymphoma and a normal person.

Example 11. Metagenomic Analysis of Vesicles Derived from Blood Bacteria of Patient with Lymphoma After a metagenomic analysis was performed on blood from 63 patients with lymphoma and 53 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with lymphoma as compared to the blood from the normal persons (see Table 14 and FIG. 10).

TABLE 14

| Blood | Control | | Lymphoma | | t-test | |
|---|---|---|---|---|---|---|
| Taxon | Mean | SD | Mean | SD | p-value | Ratio |
| g_Morganella | 0.0005 | 0.0030 | 0.0000 | 0.0000 | 0.1967 | 0.00 |

Figure 11:
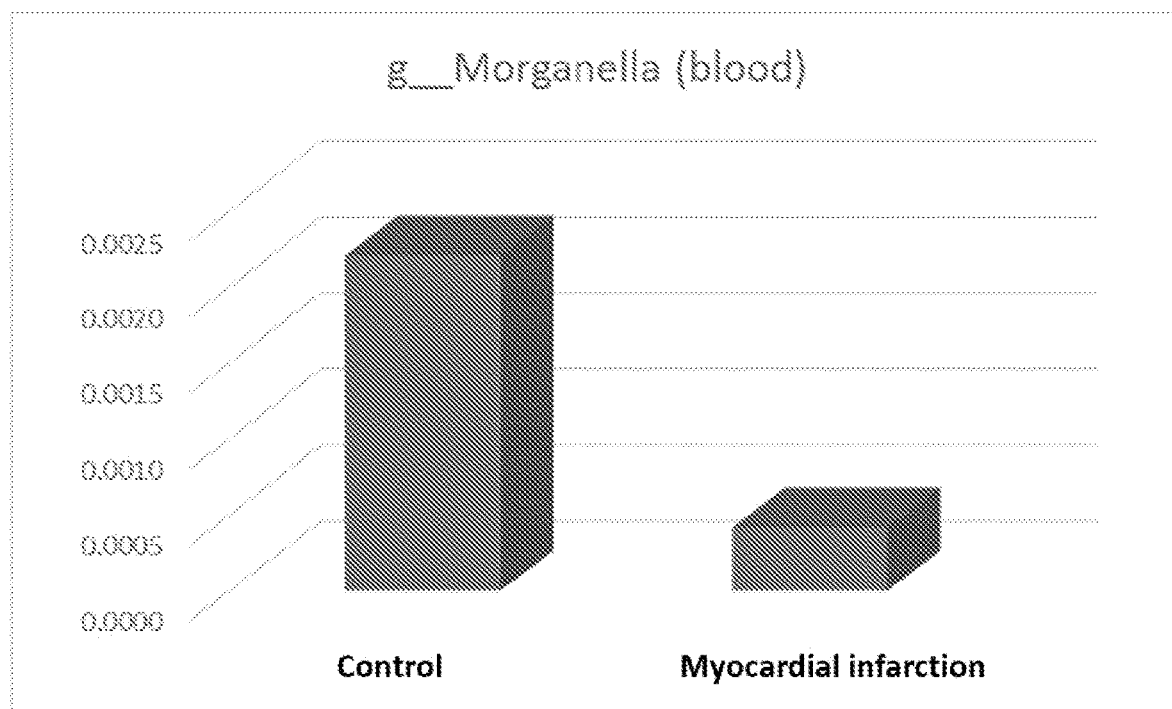
FIG. 11 is a result of comparing the distributions of vesicles derived from genus *Morganella* bacteria after performing a metagenomic analysis on vesicles derived from bacteria present in the blood of a patient with myocardial infarction and a normal person.

Example 12. Metagenomic Analysis of Vesicles Derived from Blood Bacteria of Patient with Heart Disease After a metagenomic analysis was performed on blood from 57 patients with myocardial infarction and 163 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with myocardial infarction as compared to the blood from the normal persons (see Table 15 and FIG. 11).

TABLE 15

| Blood | Control | | Myocardial infarction | | t-test | |
|---|---|---|---|---|---|---|
| Taxon | Mean | SD | Mean | SD | p-value | Ratio |
| g_Morganella | 0.0022 | 0.0103 | 0.0004 | 0.0022 | 0.0400 | 0.19 |

Figure 12:
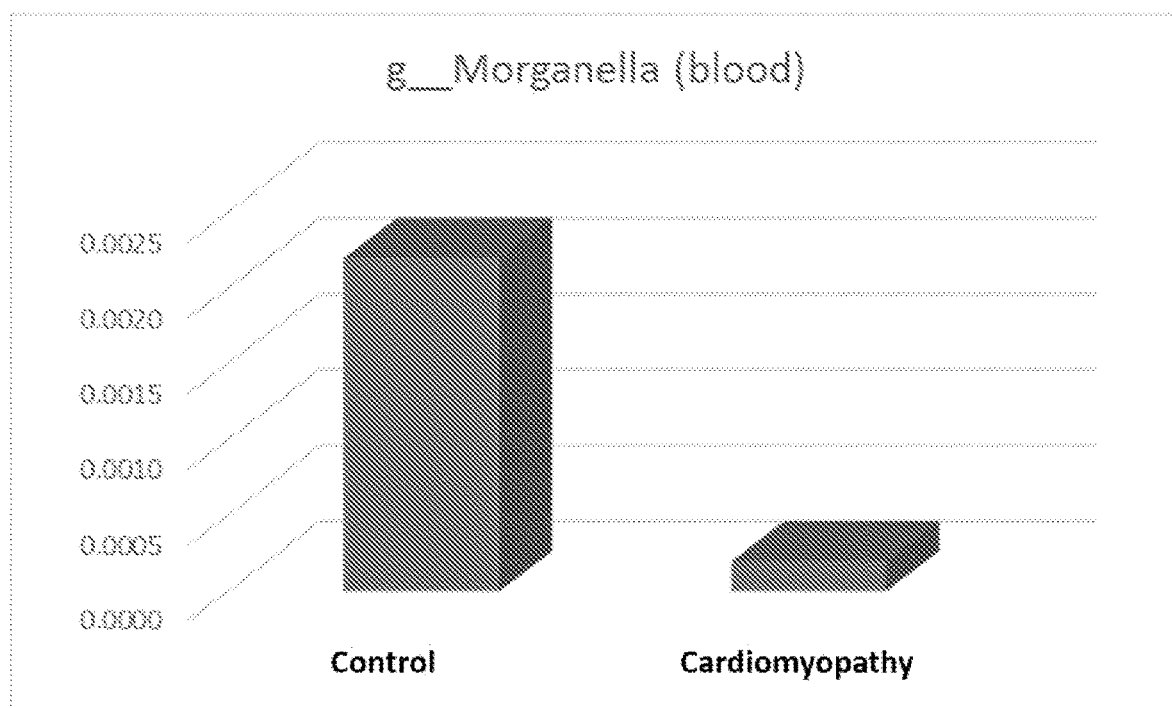
FIG. 12 is a result of comparing the distributions of vesicles derived from genus *Morganella* bacteria after performing a metagenomic analysis on vesicles derived from bacteria present in the blood of a patient with dilated cardiomyopathy and a normal person.

Further, after a metagenomic analysis was performed on blood from 72 patients with dilated cardiomyopathy and 163 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with dilated cardiomyopathy as compared to the blood from the normal persons (see Table 16 and FIG. 12).

TABLE 16

| Blood | Control | | Cardiomyopathy | | t-test | |
|---|---|---|---|---|---|---|
| Taxon | Mean | SD | Mean | SD | p-value | Ratio |
| g_Morganella | 0.0022 | 0.0104 | 0.0002 | 0.0006 | 0.0133 | 0.08 |

Figure 13:
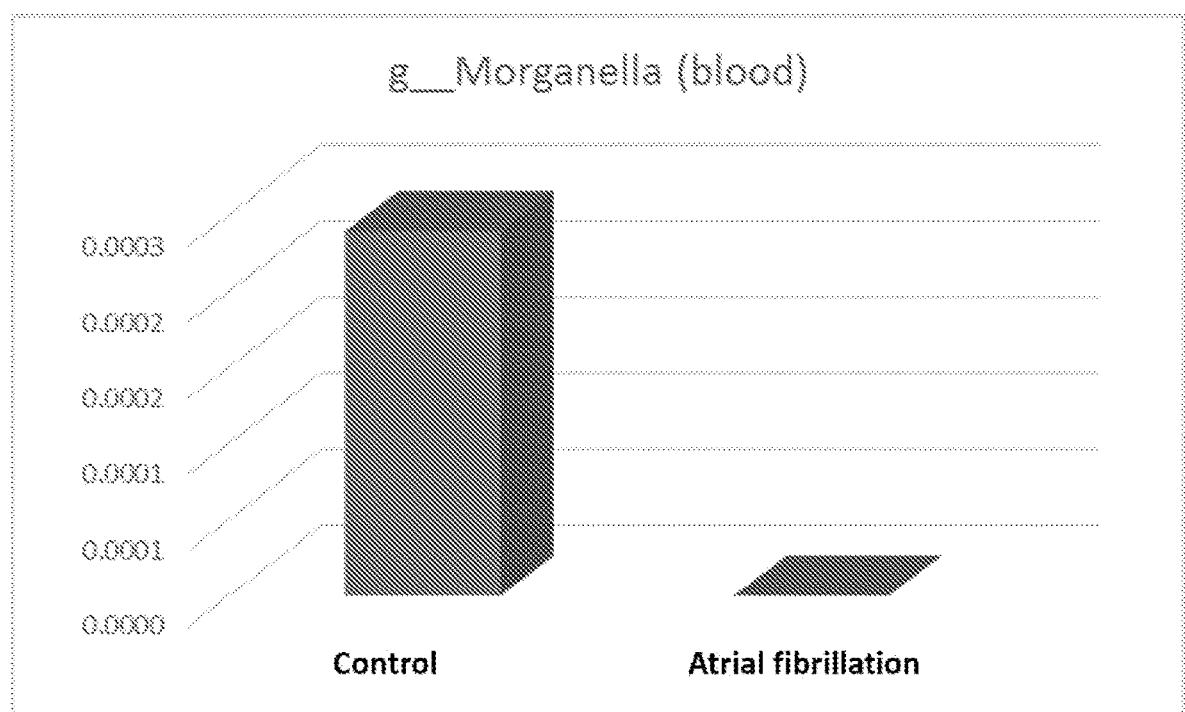
FIG. 13 is a result of comparing the distributions of vesicles derived from genus *Morganella* bacteria after performing a metagenomic analysis on vesicles derived from bacteria present in the blood of a patient with atrial fibrillation and a normal person.

Further, after a metagenomic analysis was performed on blood from 32 patients with atrial fibrillation and 32 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with atrial fibrillation as compared to the blood from the normal persons (see Table 17 and FIG. 13).

TABLE 17

| Blood | Control | | Atrial fibrillation | | t-test | |
|---|---|---|---|---|---|---|
| Taxon | Mean | SD | Mean | SD | p-value | Ratio |
| g_Morganella | 0.0002 | 0.0010 | 0.0000 | 0.0000 | 0.1774 | 0.00 |

Figure 14:
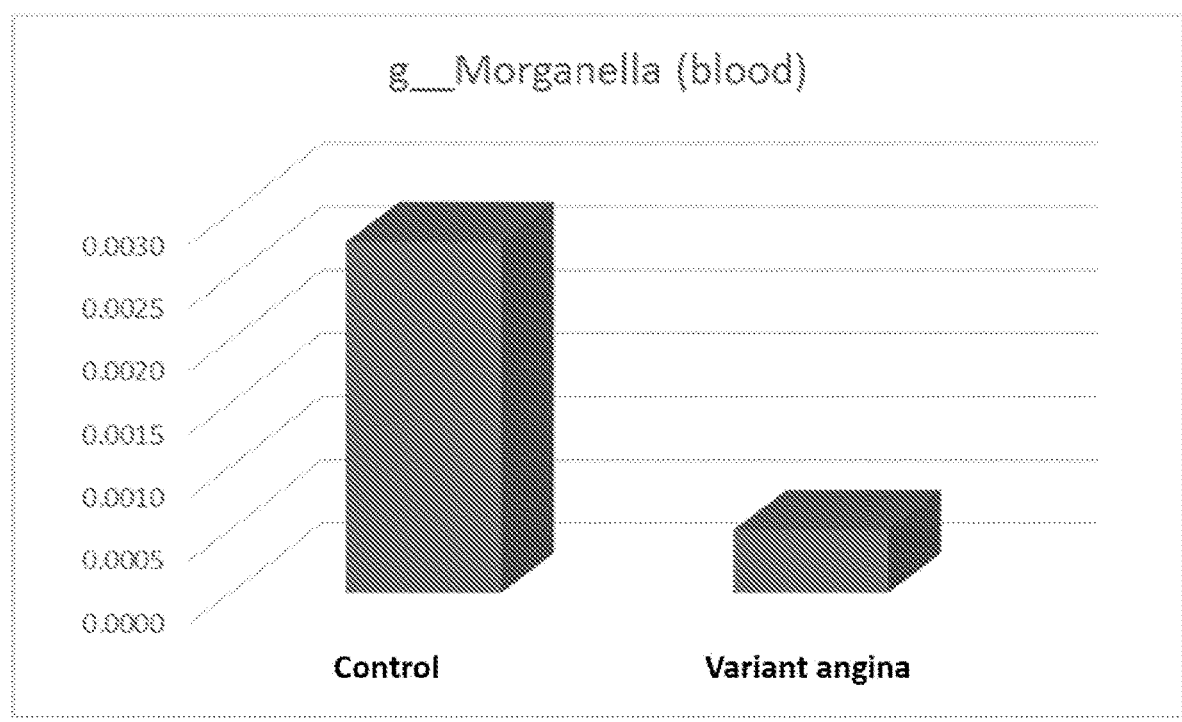
FIG. 14 is a result of comparing the distributions of vesicles derived from genus *Morganella* bacteria after performing a metagenomic analysis on vesicles derived from bacteria present in the blood of a patient with variant angina and a normal person.

Further, after a metagenomic analysis was performed on blood from 80 patients with variant angina and 80 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with variant angina as compared to the blood from the normal persons (see Table 18 and FIG. 14).

TABLE 18

| Blood | Control | | Variant angina | | t-test | |
|---|---|---|---|---|---|---|
| Taxon | Mean | SD | Mean | SD | p-value | Ratio |
| g_Morganella | 0.0028 | 0.0146 | 0.0005 | 0.0020 | 0.1736 | 0.18 |

Figure 15:
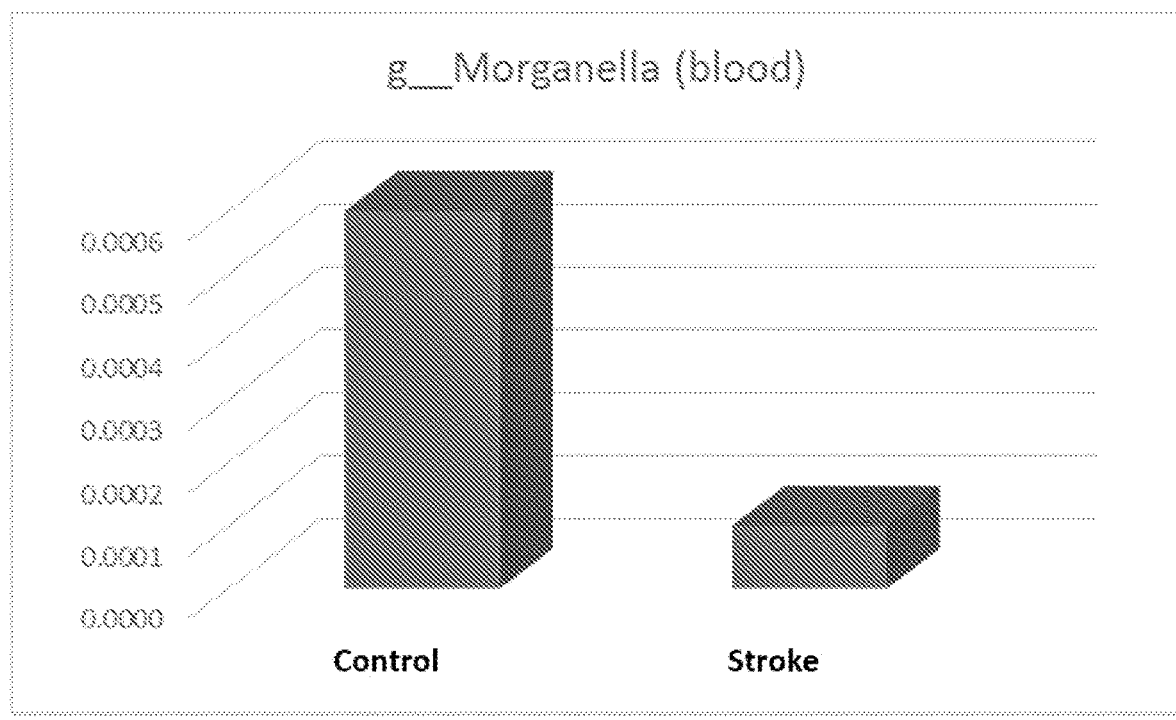
FIG. 15 is a result of comparing the distributions of vesicles derived from *Morganella* bacteria after performing a metagenomic analysis on vesicles derived from bacteria present in the blood of a patient with stroke and a normal person.

Example 13. Metagenomic Analysis of Vesicles Derived from Blood Bacteria of Patient with Stroke After a metagenomic analysis was performed on blood from 115 patients with stroke and 109 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with stroke as compared to the blood from the normal persons (see Table 19 and FIG. 15).

TABLE 19

| Blood | Control | | Stroke | | t-test | |
|---|---|---|---|---|---|---|
| Taxon | Mean | SD | Mean | SD | p-value | Ratio |
| g_Morganella | 0.0006 | 0.0028 | 0.0001 | 0.0014 | 0.1331 | 0.22 |

Figure 16A:
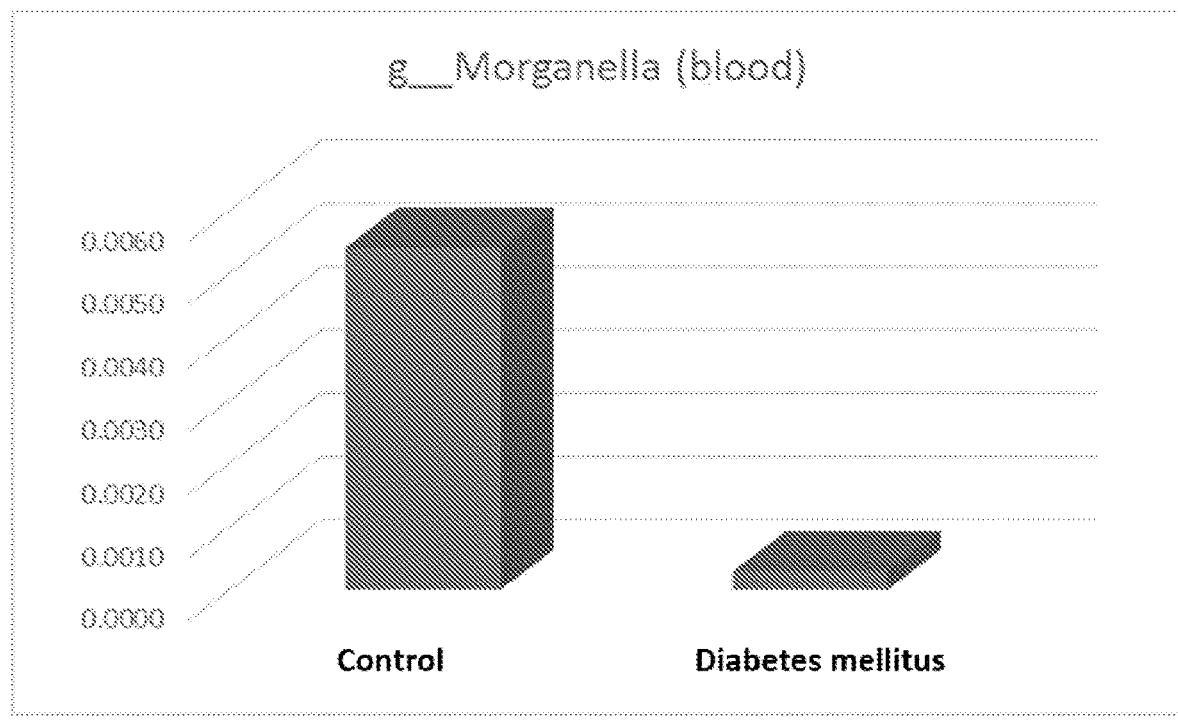
FIGS. 16A and 16B are results of comparing the distributions of vesicles derived from genus *Morganella* bacteria after performing a metagenomic analysis on vesicles derived from bacteria present in the blood (16A) and urine (16B) of a patient with diabetes mellitus and a normal person.

Example 14. Metagenomic Analysis of Vesicles Derived from Blood and Urine Bacteria of Patient with Diabetes Mellitus After a metagenomic analysis was performed on blood from 73 patients with diabetes mellitus and 146 normal persons who were matched in age and sex by extracting genes from vesicles present in the blood by the method in Example 2, the distribution of vesicles derived from genus *Morganella* bacteria was evaluated. As a result, it was confirmed that vesicles derived from genus *Morganella* bacteria were significantly decreased in the blood from the patients with diabetes mellitus as compared to the blood from the normal persons (see Table 20 and FIG. 16A).

TABLE 20

| Blood | Control | | Diabetes mellitus | | t-test | |
|---|---|---|---|---|---|---|
| Taxon | Mean | SD | Mean | SD | p-value | Ratio |
| g_Morganella | 0.0054 | 0.0177 | 0.0003 | 0.0003 | 0.0012 | 0.05 |

Figure 16B:
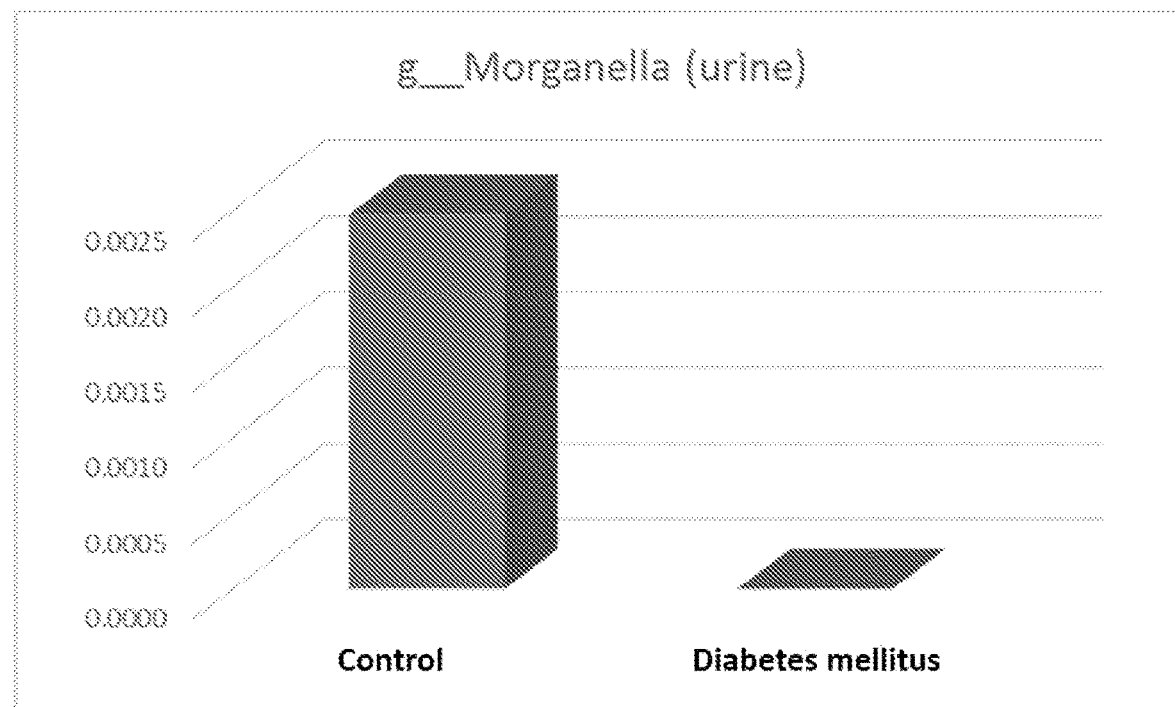

Further, after a metagenomic analysis was performed on urine from 60 patients with diabetes mellitus and 134 normal persons who were matched in age and sex by extracting genes from vesicles present in the urine by the method in Example 2, the distribution of vesicles derived from genus *Morganella* bacteria was evaluated. As a result, it was confirmed that vesicles derived from genus *Morganella* bacteria were significantly decreased in the urine from the patients with diabetes mellitus as compared to the urine from the normal persons (see Table 21 and FIG. 16B).

TABLE 21

| Urine | Control | | Diabetes mellitus | | t-test | |
|---|---|---|---|---|---|---|
| Taxon | Mean | SD | Mean | SD | p-value | Ratio |
| g_Morganella | 0.0025 | 0.0119 | 0.0000 | 0.0000 | 0.0245 | 0.00 |

Figure 17:
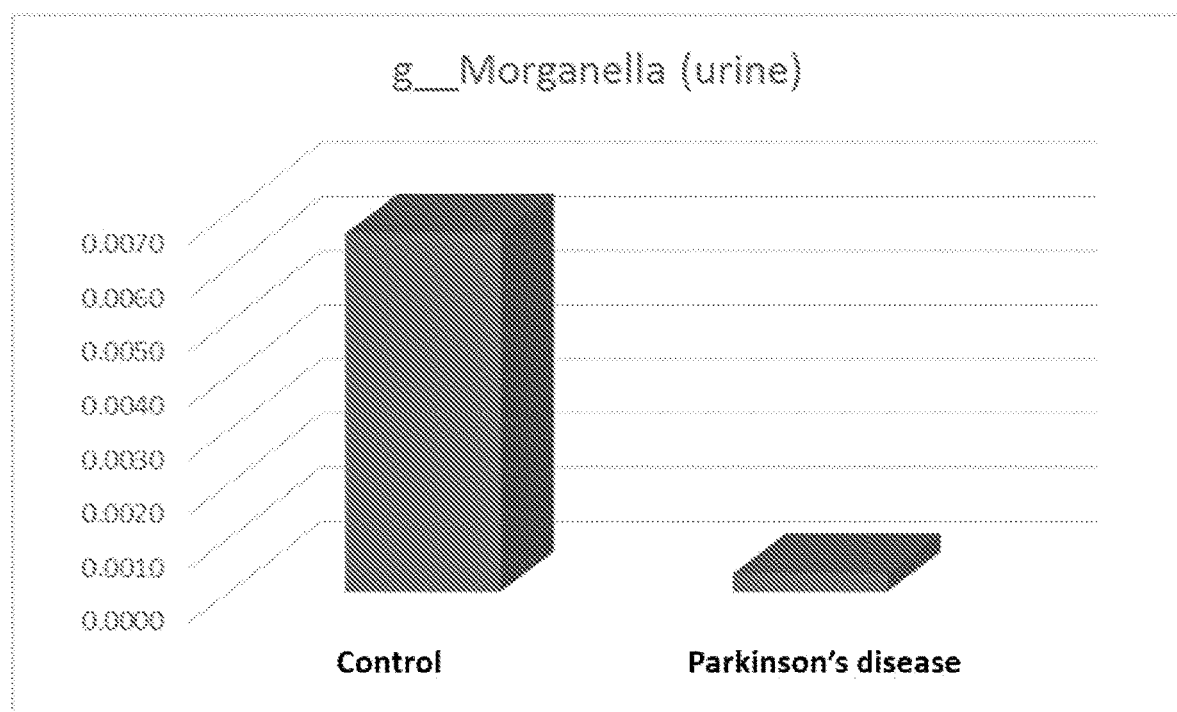
FIG. 17 is a result of comparing the distributions of vesicles derived from genus *Morganella* bacteria after performing a metagenomic analysis on vesicles derived from bacteria present in the urine of a patient with Parkinson's disease and a normal person.

Example 15. Metagenomic Analysis of Vesicles Derived from Urine Bacteria of Patient with Parkinson's Disease After a metagenomic analysis was performed on urine from 39 patients with Parkinson's disease and 79 normal persons who were matched in age and sex by extracting genes from vesicles present in the urine by the method in Example 2, the distribution of vesicles derived from genus *Morganella* bacteria was evaluated. As a result, it was confirmed that vesicles derived from genus *Morganella* bacteria were significantly decreased in the urine from the patients with Parkinson's disease as compared to the urine from the normal persons (see Table 22 and FIG. 17).

TABLE 22

| Urine | Control | | Parkinson's disease | | t-test | |
|---|---|---|---|---|---|---|
| Taxon | Mean | SD | Mean | SD | p-value | Ratio |
| g_Morganella | 0.0066 | 0.0182 | 0.0003 | 0.0008 | 0.0037 | 0.05 |

Example 16. Isolation of Vesicles from *Morganella morganii* Culturing Solution

Based on the Examples, after one standard strain (MMR101) from the Korean Culture Center of Microorganisms (KCCM) and two isolated strains (MMR201, MMR202) isolated from humans were cultured as *Morganella morganii* (*M. morganii*) strains, vesicles were isolated from the culturing solution and characteristics thereof were analyzed. The *Morganella morganii* (*M. morganii*) strains were cultured in a Luria-Bertani (LB) medium in an incubator at 37° C. until the absorbance (OD 600) became 1.0 to 1.5, and then sub-cultured. Thereafter, strains were removed by recovering the culturing solution including the strains and centrifuging the culturing solution at 10,000 g and 4° C. for 20 minutes, and the strains were filtered with a 0.22-µm filter. The filtered supernatant was concentrated to a volume of 50 ml or less through microfiltration by using a Master-Flex pump system (Cole-Parmer, US) with a 100 kDa Pellicon 2 Cassette filter membrane (Merck Millipore, US). The concentrated supernatant was filtered once again with a 0.22-µm filter. Thereafter, proteins were quantified by using a BCA assay, and the following experiments were performed on the obtained vesicles.

Example 17. Apoptotic Effects of Vesicles Derived from *Morganella morganii*

Figure 18:
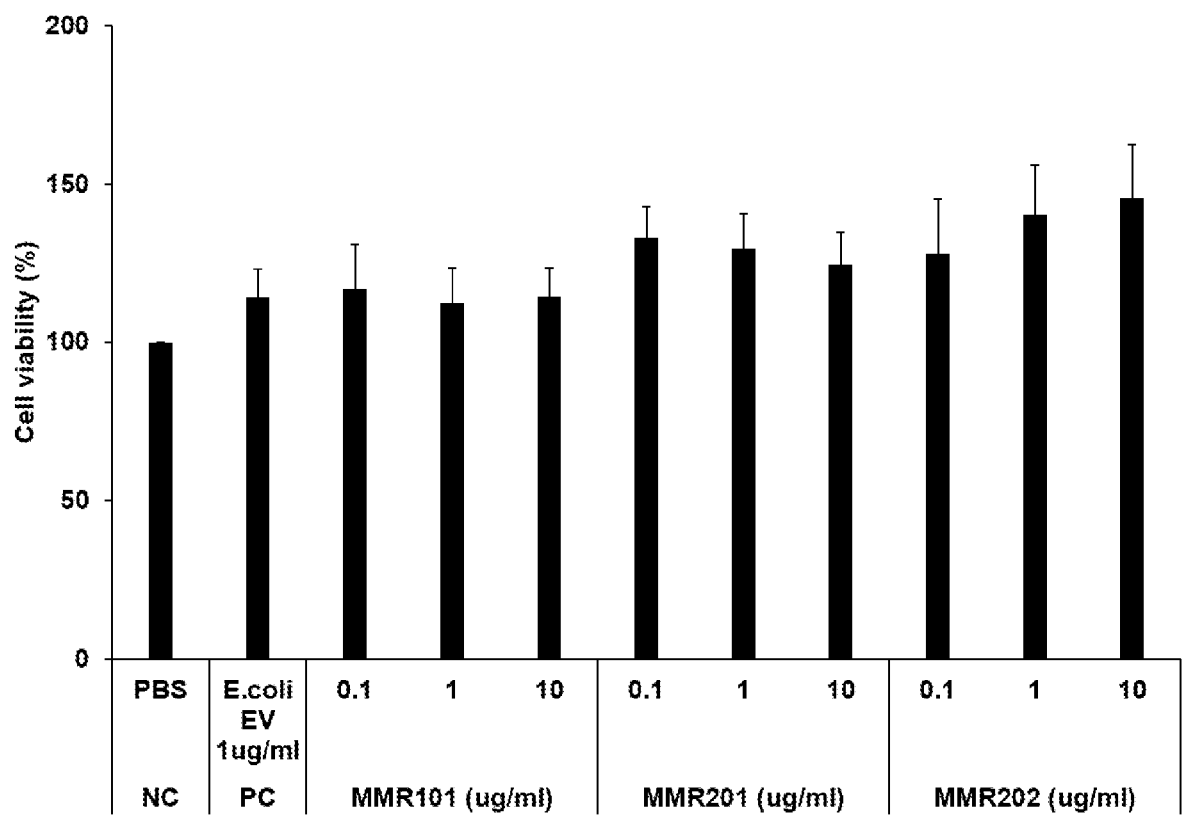
FIG. 18 is a result of evaluating apoptotic effects of vesicles derived from *Morganella morganii* by treating macrophages with the vesicles derived from *Morganella morganii* in order to evaluate the apoptotic effects of vesicles derived from *Morganella morganii*.

In order to evaluate apoptotic effects of vesicles derived from *Morganella morganii* (*M. morganii* EV) in inflammatory cells, after Raw 264.7 cells which are mouse macrophages were treated with vesicles derived from *Morganella morganii* (MMR101, MMR201, MMR202) at various concentrations (0.1, 1, 10 µg/ml), the degree of apoptosis was evaluated. More specifically, Raw 264.7 cells aliquoted at $5 \times 10^4$ cells/well into a 48-well cell culture plate were treated with vesicles derived from *Morganella morganii* (MMR101, MMR201, MMR202) at various concentrations, which was diluted with a DMEM serum-free medium, and the treated vesicles were cultured for 12 hours. Thereafter, apoptosis was measured by using EZ-CYTOX (Dogen, Korea). As a result, during the treatment with vesicles derived from *Morganella morganii* (MMR101, MMR201, MMR202), apoptosis was not observed (see FIG. 18).

Example 18. Anti-inflammatory Effects of Vesicles Derived from *Morganella morganii*

Figure 19A:
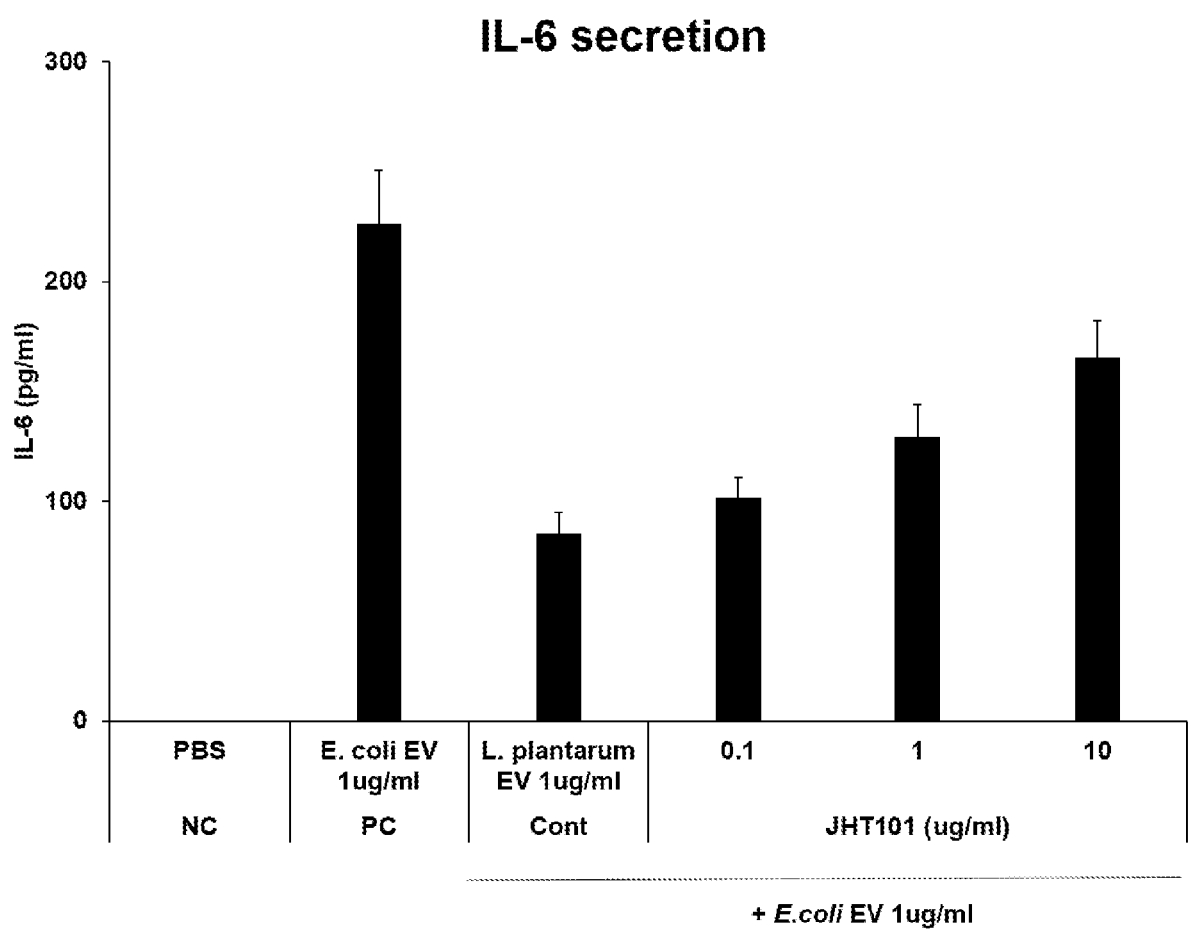
FIGS. 19A and 19B are the evaluation results of effects on secretion of inflammatory mediators, IL-6 (19a) and TNF-α (19b) by macrophage by pre-treatment of macrophage with the vesicles derived from *Morganella morganii* before treating with the pathogenic *Escherichia coli* vesicles (*E. coli* EV), to evaluate the anti-inflammatory effects of the vesicles derived from *Morganella morganii*.
Figure 19B:
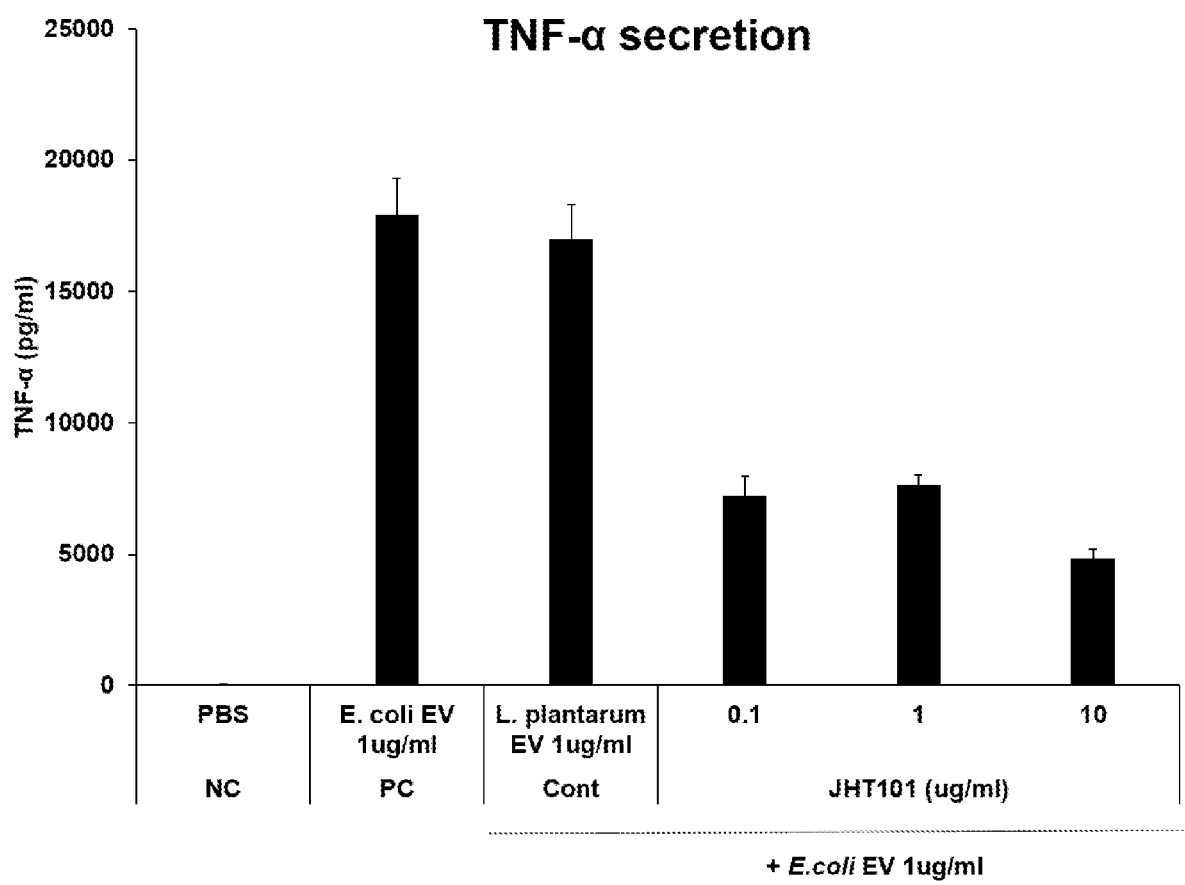
Figure 20:
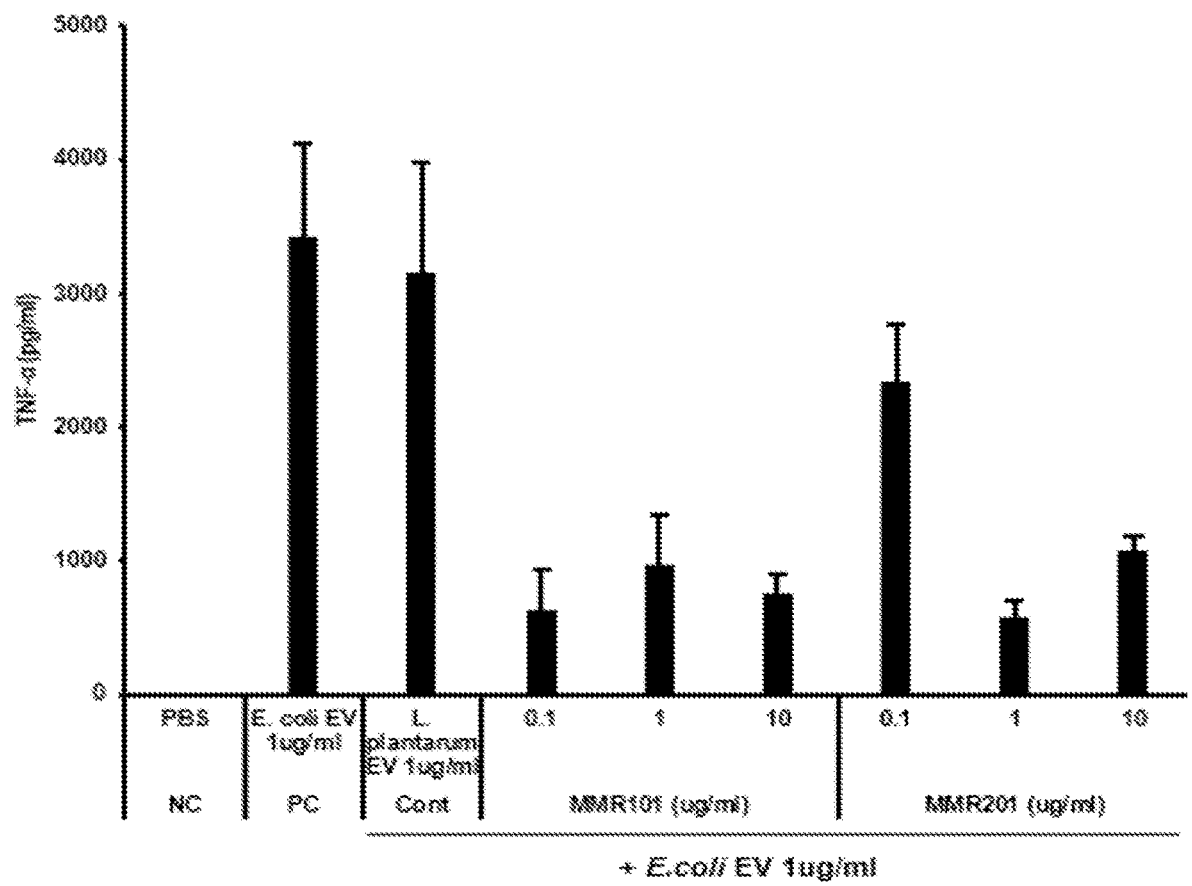
FIG. 20 is an evaluation results of effects on the secretion of TNF-α induced by *Escherichia coli* vesicles by pre-treatment of macrophage with vesicles derived from *Morganella morganii* (MMR101, MMR201) isolated from different persons before treating with the pathogenic *Escherichia coli* vesicles (*E. coli* EV) to compare the anti-inflammatory effects of vesicles derived from different strains of *Morganella morganii* (NC: negative control; PC: positive control; *L. plantarum*: *Lactobacillus plantarum*).

In order to investigate the effects of vesicles derived from *Morganella morganii* on the secretion of inflammatory mediators in inflammatory cells, after Raw 264.7 cells which are mouse macrophages were treated with vesicles derived from *Morganella morganii* (MMR101) at various concentrations (0.1, 1, 10 µg/ml), the amount of inflammatory mediators (IL-6, TNf-α, and the like) secreted was measured by treating vesicles derived from *Escherichia coli* (*E. coli* EV) which are vesicles for inflammatory disease pathogenesis. More specifically, after Raw 264.7 cells were aliquoted at $1 \times 10^5$ cells/well into a 24-well cell culture plate, the cells were cultured in a DMEM complete medium for 24 hours. Thereafter, the culture supernatant was collected in a 1.5-ml tube and centrifuged at 3,000 g for 5 minutes, the supernatant was recovered and stored at 4° C., and then an ELISA analysis was performed. As a result, it was confirmed that when the vesicles derived from *Morganella morganii* were pre-treated, the secretion of IL-6 and TNF-α by the vesicles derived from *Escherichia coli* was remarkably suppressed (see FIGS. 19A and 19B). In particular, when the vesicles derived from *Morganella morganii* were pre-treated, the degree of suppressing secretion of TNF-α in macrophages was remarkably high as compared to *Lactobacillus plantarum* vesicles (see FIG. 19B).

In order to investigate the effects of vesicles derived from *Organellar morganii* on the secretion of inflammatory mediators in inflammatory cells, Raw 264.7 cells, which are mouse macrophages, were treated with vesicles derived from *Morganella morganii* (MMR101) at various concentrations (0.1, 1, 10 µg/ml), and then the Raw 264.7 cells were treated with *E. coli* derived proinflammatory pathogenic vesicles. More specifically, after Raw 264.7 cells were aliquoted at $1 \times 10^5$ cells/well into a 24-well cell culture plate, the cells were cultured in a DMEM complete medium for 24 hours. Thereafter, the culture supernatant was collected in a 1.5-ml tube and centrifuged at 3,000 g for 5 minutes, the supernatant was recovered and stored at 4° C., and then an ELISA analysis was performed. As a result, it was confirmed that pre-treating the macrophage with the vesicles derived from *Morganella morganii*, the secretion of IL-6 and TNF-α induced by the vesicles derived from *Escherichia coli* was remarkably suppressed (see FIGS. 19A and 19B). In particular, when the macrophages were pre-treated with the vesicles derived from *Morganella morganii*, the degree of suppression of secretion of TNF-α from the macrophages was remarkably high as compared to the macrophages treated with *Lactobacillus plantarum* vesicles (see FIG. 19B).

Example 19. Effects of Heat or Acid Treatment on Anti-Inflammatory Action of Vesicles Derived from *Morganella morganii*

Figure 21:
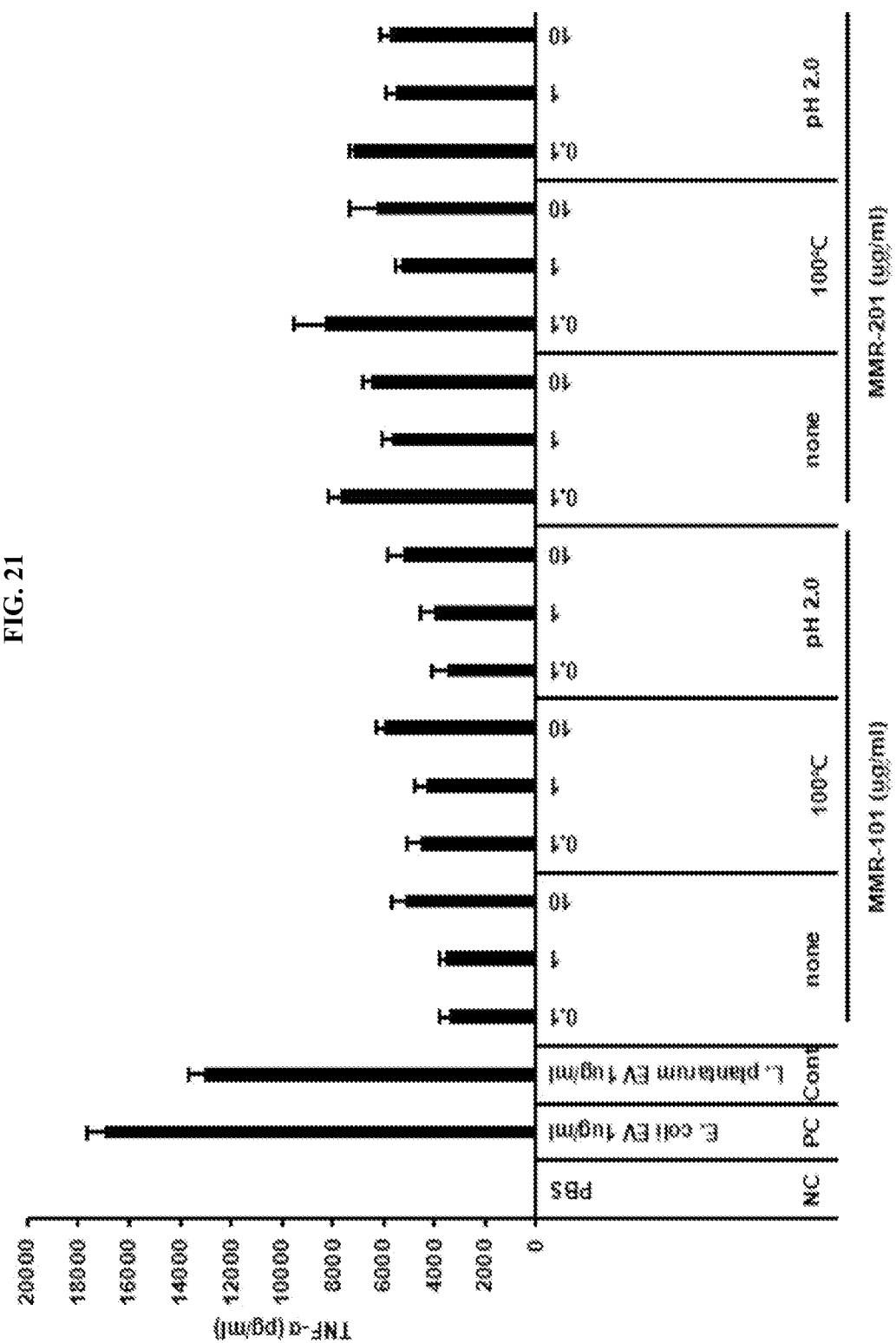
FIG. 21 is an evaluation results on the secretion of TNF-α by pre-treatment of macrophage with vesicles derived from *Morganella morganii* (MMR101, MMR201) treated with heat or acid before treating with the pathogenic *Escherichia coli* vesicles (*E. coli* EV) to evaluate effects of the heat or acid treatment on anti-inflammatory effects of vesicles derived from *Morganella morganii* (NC: negative control; PC: positive control; *L. plantarum*: *Lactobacillus plantarum*).

Through Example 18, anti-inflammatory effects of vesicles derived from the *Morganella morganii* standard strain (MMR101) and an isolation strain (MMR201) were identified, and furthermore, the stability of the vesicles and characteristics of effective materials were specifically investigated. For this purpose, anti-inflammatory effects were evaluated by pre-treating macrophages (Raw 264.7) with vesicles derived from two strains of *Morganella morganii* (MMR101, MMR201) boiled at 100° C. for 10 minutes or treated with an acid. As a result, it was confirmed that even though the vesicles were boiled at 100° C. or treated with an acid, anti-inflammatory effects of vesicles derived from *Morganella morganii* were maintained (see FIG. 21). This means that the anti-inflammatory action of vesicles derived from *Morganella morganii* is stable against temperature and acids.

Example 20. Anti-Cancer Effects of Vesicles Derived from *Morganella morganii*

Figure 22:
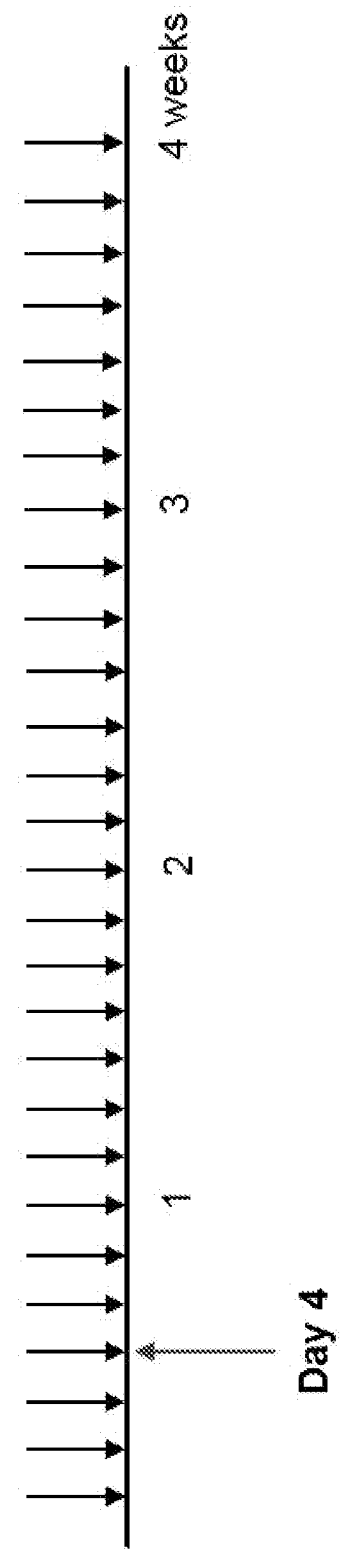
FIG. 22 is a protocol of administering vesicles derived from *Morganella morganii* to mice in order to evaluate the anticancer efficacy of vesicles derived from *Morganella morganii*.
Figure 23:
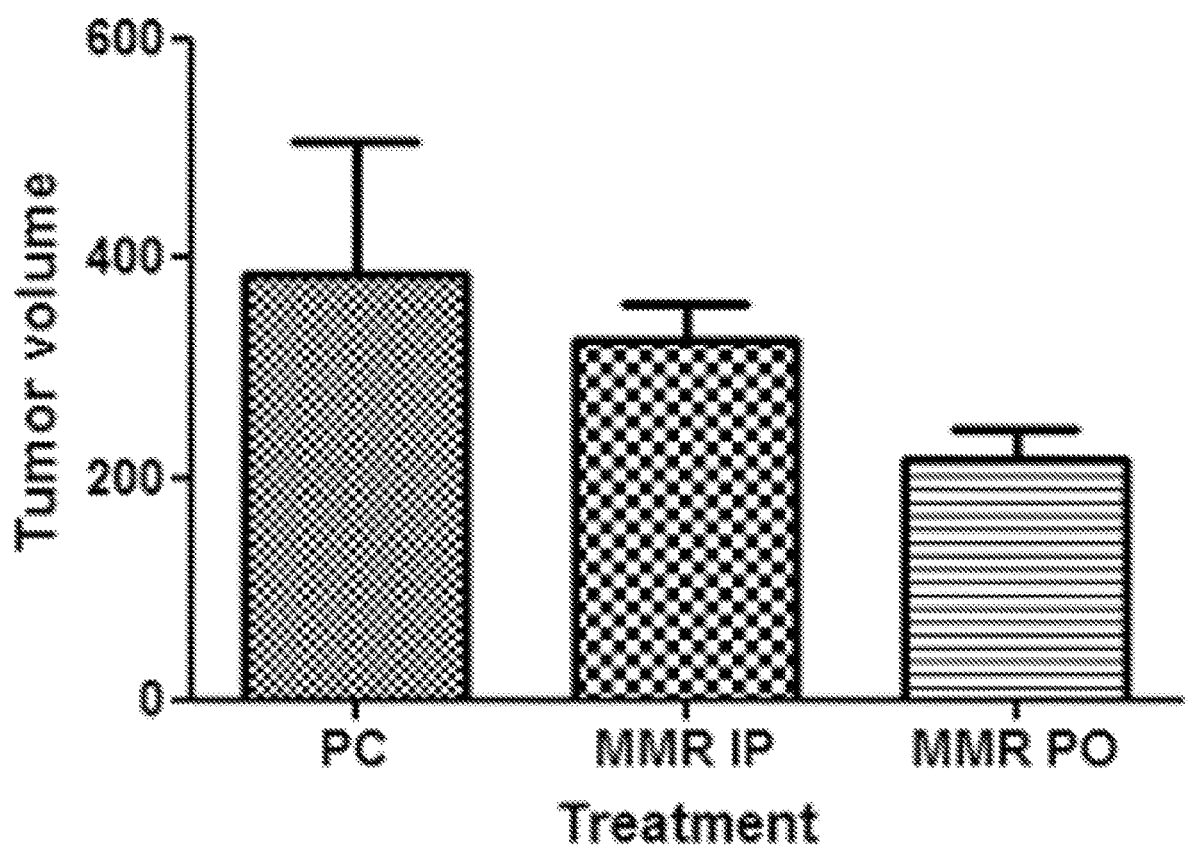
FIG. 23 is a result of evaluating effects of cancer cells on tumorigenesis by administering *Morganella morganii* vesicles intraperitoneally (IP) or orally (PO) in order to evaluate the anticancer efficacy of vesicles derived from *Morganella morganii*.

Furthermore, anti-cancer effects of vesicles derived from *Morganella morganii* were investigated based on the Examples. For this purpose, as illustrated in FIG. 22, a cancer model was prepared by intraperitoneally injecting or orally administering vesicles derived from isolated strains of *Morganella morganii* (MMR201) to 6-week old C57BL/6 male mice, and subcutaneously injecting a cancer cell line (CT26 cell) on day 4 after administration. After administration of the cancer cell line, the vesicles derived from isolated strains of *Morganella morganii* were intraperitoneally injected or orally administered daily, and the sizes of cancer tissues were measured until day 24 (see FIG. 22). As a result, the sizes of cancer tissues were decreased in mice to which the vesicles were administered through intraperitoneal injection and mice to which the vesicles were orally administered as compared to a group to which physiological saline was orally administered, which is a control, and in particular, when the vesicles were orally administered, the sizes were further decreased (see FIG. 23). This means that when vesicles derived from *Morganella morganii* are administered, the growth of cancer tissues may be efficiently suppressed.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

It is expected that vesicles derived from genus *Morganella* bacteria according to the present invention can be usefully used for a method for diagnosing gastric cancer, colorectal cancer, pancreatic cancer, bile duct cancer, breast cancer, ovarian cancer, bladder cancer, prostate cancer, lymphoma, myocardial infarction, cardiomyopathy, atrial fibrillation, variant angina, stroke, diabetes mellitus, and Parkinson's disease, and a composition for prevention or treatment, such as a food or drug, of the diseases or an inflammatory disease.

The invention claimed is:

1. A method for treating a colorectal cancer, comprising administering a composition comprising vesicles derived from *Morganella morganii* bacteria as an active ingredient, to the subject.

2. The method of claim 1, wherein the vesicles have an average diameter of 10 to 200 nm.

3. The method of claim 1, wherein the vesicles are secreted naturally or artificially from the *Morganella morganii* bacteria.

4. The method of claim 1, wherein the composition is administered in combination with other therapeutic agents.

5. The method of claim 1, wherein the composition and other therapeutic agents are administered sequentially or simultaneously.

6. A composition for alleviating or treating colorectal cancer, comprising an effective amount of vesicles derived from *Morganella morganii* bacteria as an active ingredient.

7. The composition of claim 6, wherein the composition is a pharmaceutical composition or food composition.

8. The method of claim 1, wherein the composition is administered orally or by injection.

9. The method of claim 1, wherein the composition is administered daily or every other day.

10. The composition of claim 6, wherein the composition is a pharmaceutical composition.

* * * * *